US 6,672,458 B2

(12) United States Patent
Hansen et al.

(10) Patent No.: US 6,672,458 B2
(45) Date of Patent: Jan. 6, 2004

(54) SYSTEM AND METHOD FOR MANIPULATING MAGNETICALLY RESPONSIVE PARTICLES FLUID SAMPLES TO COLLECT DNA OR RNA FROM A SAMPLE

(75) Inventors: Timothy Roy Hansen, Spring Grove, PA (US); Bradley Scott Thomas, Timonium, MD (US); John Joseph Bianco, Baltimore, MD (US); Matthew P. Collis, Seven Valley, PA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 62 days.

(21) Appl. No.: 09/858,889

(22) Filed: May 17, 2001

(65) Prior Publication Data
US 2002/0014443 A1 Feb. 7, 2002

Related U.S. Application Data

(63) Continuation-in-part of application No. 09/573,540, filed on May 19, 2000.

(51) Int. Cl.[7] .......................... G01N 33/487; B03C 1/00
(52) U.S. Cl. ........................ 209/224; 210/222; 210/695; 73/61.42; 422/101; 436/526
(58) Field of Search ....................... 209/224; 436/526; 210/222, 695; 422/101; 73/61.42

(56) References Cited

U.S. PATENT DOCUMENTS

| 4,272,510 A | * | 6/1981 | Smith et al. | 427/598 |
|---|---|---|---|---|
| 4,438,068 A | | 3/1984 | Forrest | 422/61 |
| 4,895,650 A | * | 1/1990 | Wang | 210/222 |
| 4,936,687 A | * | 6/1990 | Lilja et al. | 366/143 |
| 5,154,082 A | * | 10/1992 | Mintz | 73/64.41 |
| 5,200,084 A | * | 4/1993 | Liberti et al. | 210/695 |
| 5,443,791 A | * | 8/1995 | Cathcart et al. | 422/65 |
| 5,458,785 A | * | 10/1995 | Howe et al. | 210/695 |
| 5,498,550 A | * | 3/1996 | Fujiwara et al. | 436/526 |
| 5,567,326 A | * | 10/1996 | Ekenberg et al. | 210/695 |
| 5,622,831 A | * | 4/1997 | Liberti et al. | 435/7.21 |
| 5,681,478 A | | 10/1997 | Lea et al. | 210/695 |
| 5,684,712 A | | 11/1997 | Goffe et al. | 364/502 |
| 5,686,271 A | * | 11/1997 | Mian et al. | 435/91.1 |
| 5,698,450 A | * | 12/1997 | Ringrose et al. | 436/526 |

(List continued on next page.)

FOREIGN PATENT DOCUMENTS

| EP | 0 905 520 A1 | | 3/1999 | G01N/35/00 |
|---|---|---|---|---|
| WO | WO 91/09308 | * | 6/1991 | B03C/1/28 |
| WO | WO 91/12079 | | 8/1991 | B03C/1/00 |
| WO | WO 96/09550 | | 3/1996 | G01N/33/553 |

Primary Examiner—Donald P. Walsh
Assistant Examiner—Daniel K Schlak
(74) Attorney, Agent, or Firm—Allan M. Kiang

(57) ABSTRACT

A system and method for manipulating magnetically responsive particles in a solution to separate nucleic acid molecules from cell components in a cell solution. The system and method employ a device capable of receiving a plurality of tubes, each of which contain respective sample and magnetically responsive particles. The device includes heating and cooling devices to facilitate a lysing step to release the nucleic acid molecules from the cells in the cell solution. The device further includes moveable magnets which can be moved proximate to and away from the tube to hold the magnetically responsive particles to which the nucleic acid molecules become bound, so that the molecule-bound particles can be separated from the remainder of the solution, and washed as appropriate. The system also employs an electromagnet which is capable of demagnetizing the particles to allow the particles to freely mix with solution, such as elution solutions which are used to unbind the molecules from the particles.

16 Claims, 20 Drawing Sheets

U.S. PATENT DOCUMENTS

| | | | |
|---|---|---|---|
| 5,705,062 A | * | 1/1998 | Knobel .................... 210/205 |
| 5,770,461 A | * | 6/1998 | Sakazume et al. .......... 436/526 |
| 5,776,784 A | * | 7/1998 | Kegelman et al. .......... 436/526 |
| 5,779,907 A | * | 7/1998 | Yu ............................. 210/695 |
| 5,804,067 A | | 9/1998 | McDonald et al. ......... 210/222 |
| 5,834,197 A | * | 11/1998 | Parton ........................... 435/6 |
| 5,835,329 A | * | 11/1998 | Sucholeiki ................. 361/143 |
| 5,837,144 A | * | 11/1998 | Bienhaus et al. ........... 210/695 |
| 5,888,835 A | * | 3/1999 | Bushnell et al. ............ 436/526 |
| 6,033,574 A | | 3/2000 | Siddiqi ...................... 210/695 |
| 6,090,935 A | | 7/2000 | Breivik et al. ............. 536/25.4 |
| 6,117,398 A | * | 9/2000 | Bienhaus et al. ........... 422/101 |
| 6,228,268 B1 | * | 5/2001 | Siddiqi ...................... 210/695 |
| 6,294,342 B1 | | 9/2001 | Rohr et al. |
| 6,312,910 B1 | * | 11/2001 | Vellinger et al. ............... 435/6 |
| 6,346,196 B1 | * | 2/2002 | Bose ......................... 210/695 |
| 6,368,561 B1 | * | 4/2002 | Rutishauser et al. .......... 422/99 |

* cited by examiner

SYSTEM AND METHOD FOR MANIPULATING MAGNETICALLY RESPONSIVE PARTICLES FLUID SAMPLES TO COLLECT DNA OR RNA FROM A SAMPLE

This is a continuation-in-part of U.S. patent application Ser. No. 09/573,540, filed May 19, 2000, now abandoned, the entire content of which is incorporated herein by reference.

BACKGROUND OF THE INVENTION

1. Field of the Invention

The present invention relates to a system and method for manipulating magnetic particles in a fluid sample to efficiently and effectively collect DNA or RNA that has been bound to the particles. More particularly, the present invention relates to a system and method employing movable magnets for holding and releasing magnetic particles in a fluid sample so that DNA or RNA bound to the magnetic particles can be separated from the fluid sample.

2. Description of the Related Art

A variety of molecular biology methodologies, such as nucleic acid sequencing, direct detection of particular nucleic acids sequences by nucleic acid hybridization, and nucleic acid sequence amplification techniques, require that the nucleic acids (DNA or RNA) be separated from the remaining cellular components. This process generally includes the steps of collecting the cells in a sample tube and lysing the cells with heat and reagent which causes the cells to burst and release the nucleic acids (DNA or RNA) into the solution in the tube. The tube is then placed in a centrifuge, and the sample is spun down so that the various components of the cells are separated into density layers within the tube. The layer of the nucleic acids can be removed from the sample by a pipette or any suitable instrument. The samples can then be washed and treated with appropriate reagents, such as fluorescein probes, so that the nucleic acids can be detected in an apparatus such as the BDProbeTec™ ET system, manufactured by Becton Dickinson and Company and described in U.S. Pat. No. 6,043,880 to Andrews et al., the entire contents of which is incorporated herein by reference. Although the existing techniques for separating nucleic acids from cell samples may be generally suitable, such methods are typically time consuming and complex. Furthermore, although the centrifuging process is generally effective in separating the nucleic acids from the other cell components, certain impurities having the same or similar density as the nucleic acids can also be collected in the nucleic acid layer, and must be removed from the cell sample with the nucleic acids.

A technique has recently been developed which is capable of more effectively separating nucleic acids from the remaining components of cells. This technique involves the use of paramagnetic particles, and is described in U.S. Pat. No. 5,973,138 to Mathew P. Collis, the entire contents of which is incorporated herein by reference.

In this technique, paramagnetic particles are placed in a buffer solution along with cell samples. After the cell samples are lysed to release the nucleic acids, a acidic solution is mixed with the particles and the nucleic acids are reversibly bound to the paramagnetic particles. The paramagnetic particles can then be separated from the remainder of the solution by known techniques such as centrifugation, filtering or magnetic force. The paramagnetic particles to which the nucleic acids are bound can then be removed from the solution and placed in an appropriate buffer solution, which causes the nucleic acids to become unbound from the magnetic particles. The paramagnetic particles can then be separated from the nucleic acids by any of the techniques described above.

Examples of systems and method for manipulating magnetic particles are described in U.S. Pat. Nos. 3,988,240, 4,895,650, 4,936,687, 5,681,478, 5,804,067 and 5,567,326, in European Patent Application No. EP905520A1, and in published PCT Application WO 96/09550, the entire contents of each of said documents being incorporated herein by reference.

Although the mangnetic or paramagnetic particle manipulating techniques can be effective in separating and harvesting nucleic acids from cell samples, a need exists for an improved technique for manipulating the magnetic or paramagnetic particles to provide an even more effective method of separation.

SUMMARY OF THE INVENTION

An object of the present invention is to provide an improved system and method for manipulating magnetically responsive particles, such as iron oxide particles, magnetic, ferromagnetic or paramagnetic particles, or any other particles that are responsive to a magnetic field, to which nucleic acid molecules are bound in a solution to effectively separate the nucleic acid molecules from the remaining components of the solution.

A further object of the present invention is to provide a system and method that is capable of altering the temperature of a cell solution to perform a lysing technique which enables nucleic acid molecules to become bound to magnetically responsive particles in the solution, as well as being capable of manipulating the magnetically responsive particles to appropriately separate the nucleic acid molecules from the remaining components of the solution.

A further object of the present invention is to provide a system and method for use in a nucleic acid assay preparation system, that is capable of heating and cooling sample solutions as appropriate to perform a lysing technique, and which is further capable of manipulating magnetically responsive particles to which nucleic acid molecules of the lysed cell samples become bound, so that the assay preparation system can properly wash the nucleic acid molecules and place the nucleic acid molecules in a sample assay.

These and other objects are substantially achieved by providing a system and method for manipulating nucleic acid molecule-bound magnetically responsive particles in a sample solution to separate the molecules from the remaining components in the solution. The system and method includes a tube receiver for receiving at least one sample tube containing a cell solution, magnetically responsive particles such as iron oxide particles, and an acidic solution. The tube receiver is adapted for use with a system for preparing nucleic acid assays. The tube receiver includes a heating and cooling unit, such as a thermoelectric element, which is capable of heating the cell solution to lyse the cell and enable the nucleic acid molecules to become bound to the magnetically responsive particles. The thermoelectric elements can also be used to quickly cool the solution as necessary. The tube receiver further includes movable magnets which can be moved proximate to the outer wall of the tubes to attract the molecule-bound magnetically responsive particles to the sides of the tubes, while the assay preparation system removes the remainder of the cell solution and washes the particles. The movable magnets can then be moved away from the tubes so that the molecule-bound magnetically responsive particles are released from the walls of the tubes, so that the assay preparation system can eject an elution reagent, such as a suitable buffer solution, which causes the nucleic acid molecules to become unbound from the magnetically responsive particles. The tube receiver further includes electromagnets which are activated to provide an alternating magnetic field to the tubes to degauss the magnetically responsive particles to allow the magnetically responsive particles to mix with the elution reagent. The movable magnets can then be moved proximate to the sample tubes to adhere the magnetically responsive particles to the walls of the sample tubes while the assay preparation system aspirates the nucleic acid molecules from the sample tubes. The assay preparation system can then place the nucleic acid molecules in the appropriate microtiter trays for reading by an assay reading system.

BRIEF DESCRIPTION OF THE DRAWINGS

These and other objects, advantages and novel features of the invention will be more readily appreciated from the following detailed description when read in conjunction with the accompanying drawings, in which.

DETAILED DESCRIPTION OF THE PREFERRED EMBODIMENTS

Figure 1:
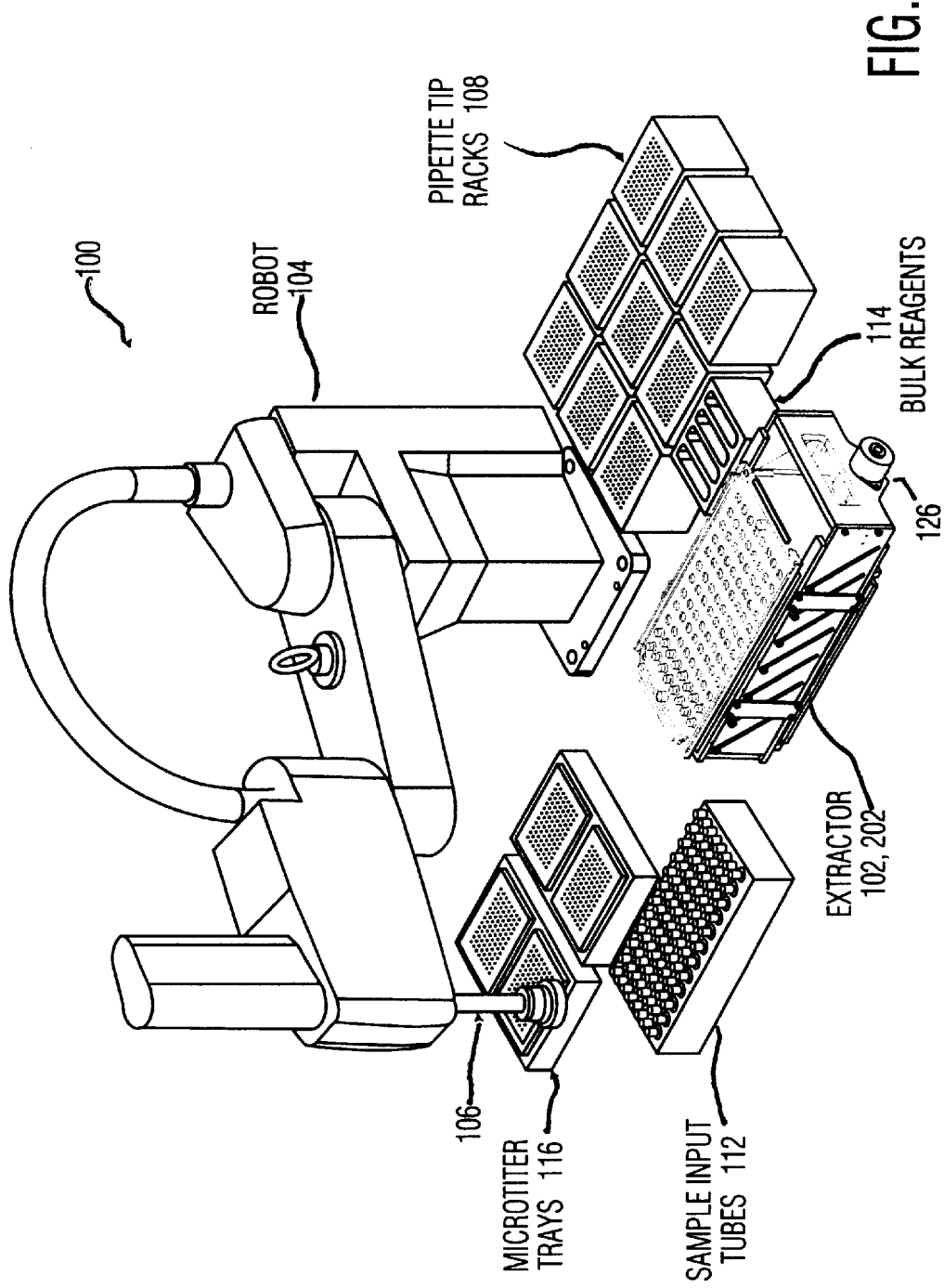
FIG. 1 is a diagram of an example of a nucleic acid assay preparation system employing a nucleic acid molecule extractor according to an embodiment of the present invention.
Figure 2:
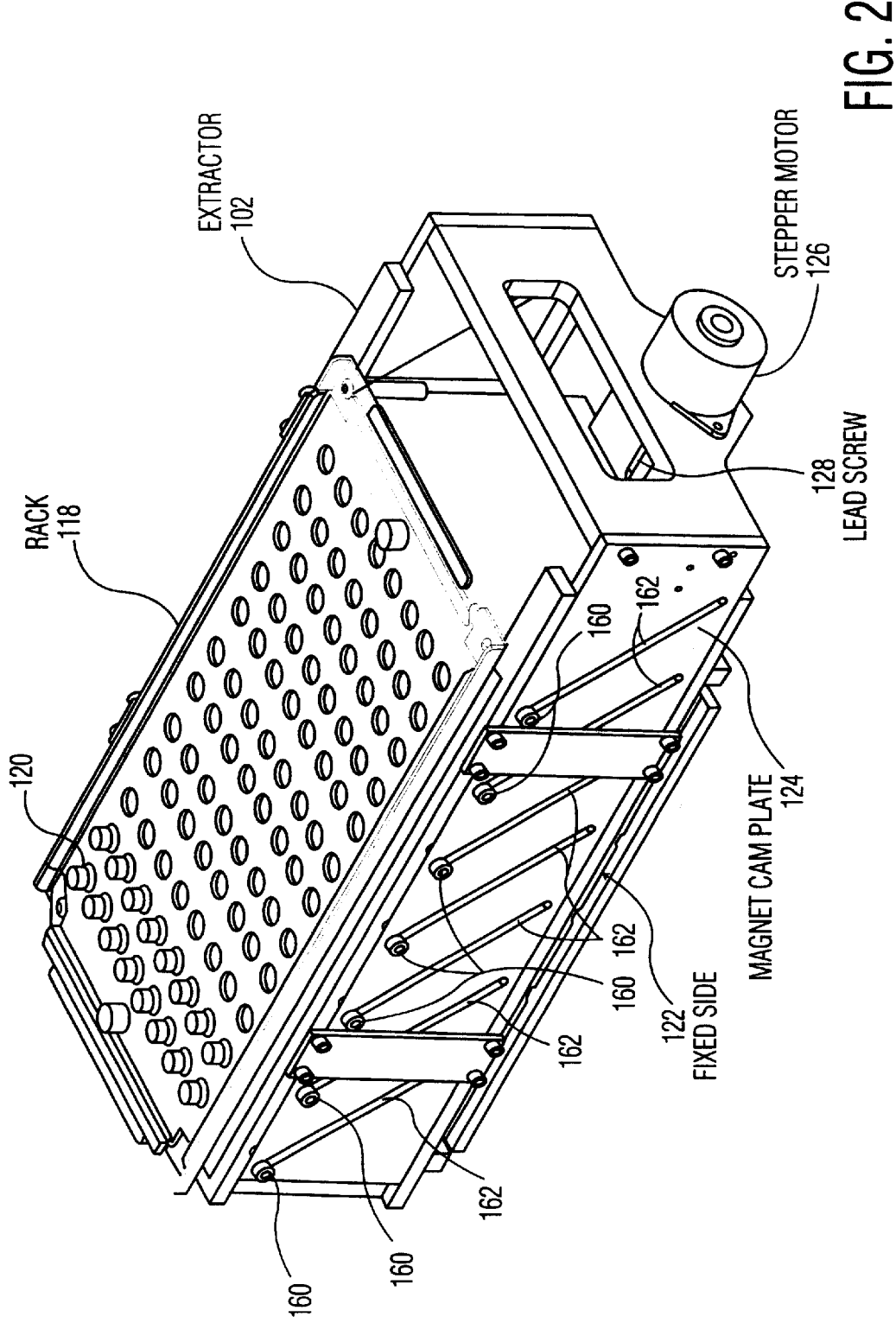
FIG. 2 is a perspective view of the nucleic acid molecule extractor shown in FIG. 1.
Figure 3:
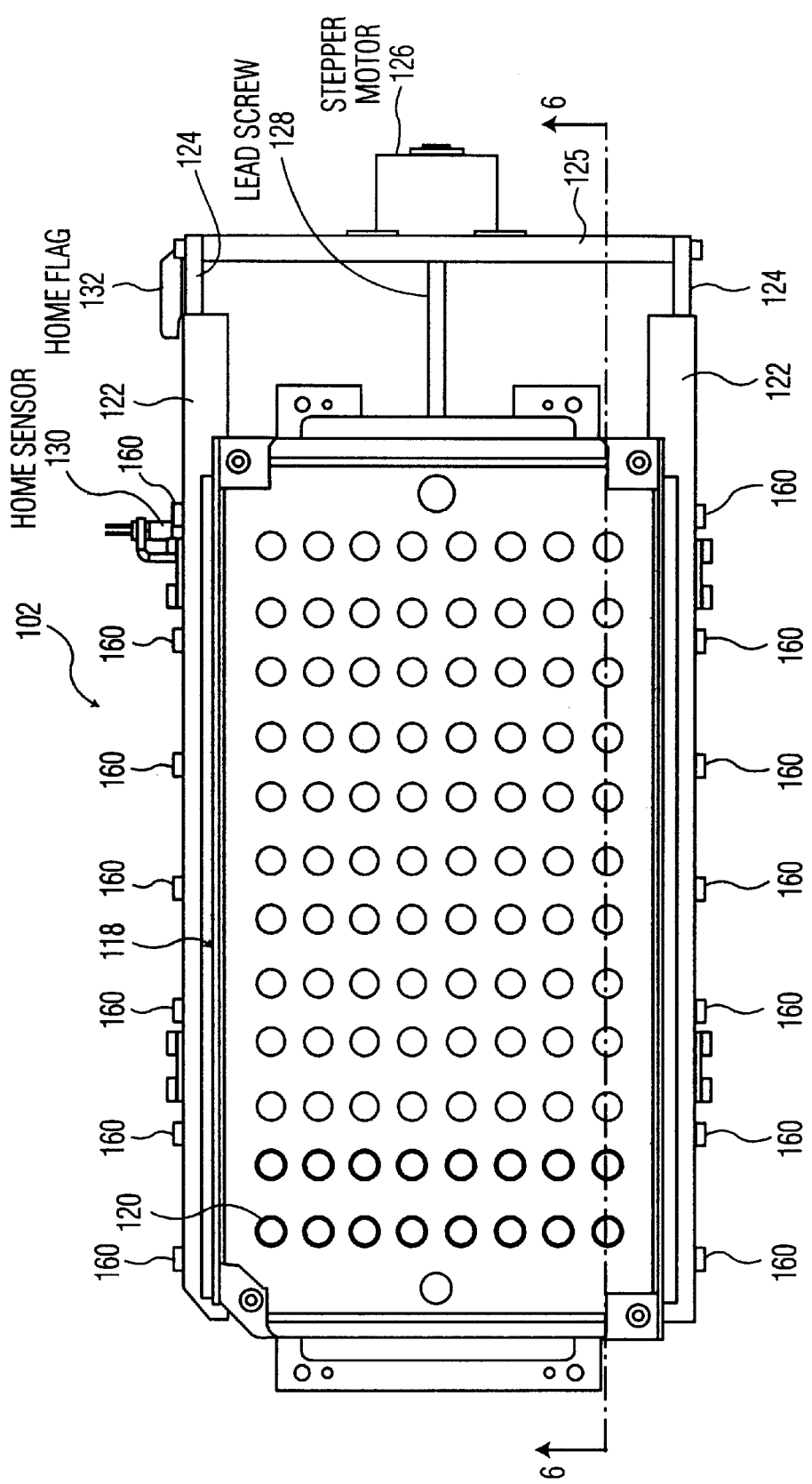
FIG. 3 is a top view of the nucleic acid molecule extractor shown in FIG. 2.

FIG. 1 illustrates a sample assay preparation system 100 for which a nucleic acid molecule extractor 102 is adapted for use. The system 100 includes a robot 104, such as a robot manufactured by Adept Corp. of San Jose, Calif., or any other suitable robot. The robot includes a pipette holding mechanism 106, which can releasably couple to a plurality of pipette tips (not shown) stored in pipette tip racks 108. The robot 104 further includes a suction mechanism (not shown) that can be activated to create a vacuum to draw fluid into the pipette tips, or to create pressure to eject fluid from the pipette tips for reasons discussed in more detail below.

As further shown in FIG. 1, a plurality of sample input tubes 112 in a sample tube holder are positioned at a predetermined location with respect to the area of movement of the robot 104. In addition, bulk reagent containers 114, which include different reagents as discussed in more detail below, and a plurality of microtiter trays 116 are located at predetermined position with respect to the robot 104.

Further details of the extractor 102 are shown in FIGS. 2–9 as will now be discussed. The extractor 102 includes a removable rack 118 into which can be placed a plurality of tubes 120 containing magnetically responsive particles such as iron oxide or those described in U.S. Pat. No. 5,973,138 referenced above. For purposes of this description, the term "magnetically responsive particles" refers to iron oxide particles, magnetic particles, ferromagnetic particles, paramagnetic particles particles, any of these types of particles that have been coated with a polymer coating, any particle described in U.S. Pat. No. 5,973,138, or any particle that is responsive to a magnetic field. In this example, each tube 120 has a 2 mL capacity and contains a dried down slurry of iron oxide particles and potassium hydroxide.

The extractor 102 further includes fixed sides 122 and cam plates 124 which extend parallel or substantially parallel to fixed sides 122 as shown. The extractor further includes a stepper motor 126 connected to a lead screw 128 which is controlled by a controller (not shown) of the system 100 to slide the cam plates 124 with respect to the fixed sides 122 for reasons discussed in more detail below. As shown, in particular, in FIG. 3, the extractor 102 includes a home sensor 130 that is connected to the controller (not shown). The home sensor detects the position of a home flag 132 to indicate to the controller the position of the cam plates 124 with respect to the fixed sides 122 for reasons discussed below.

Figure 4:
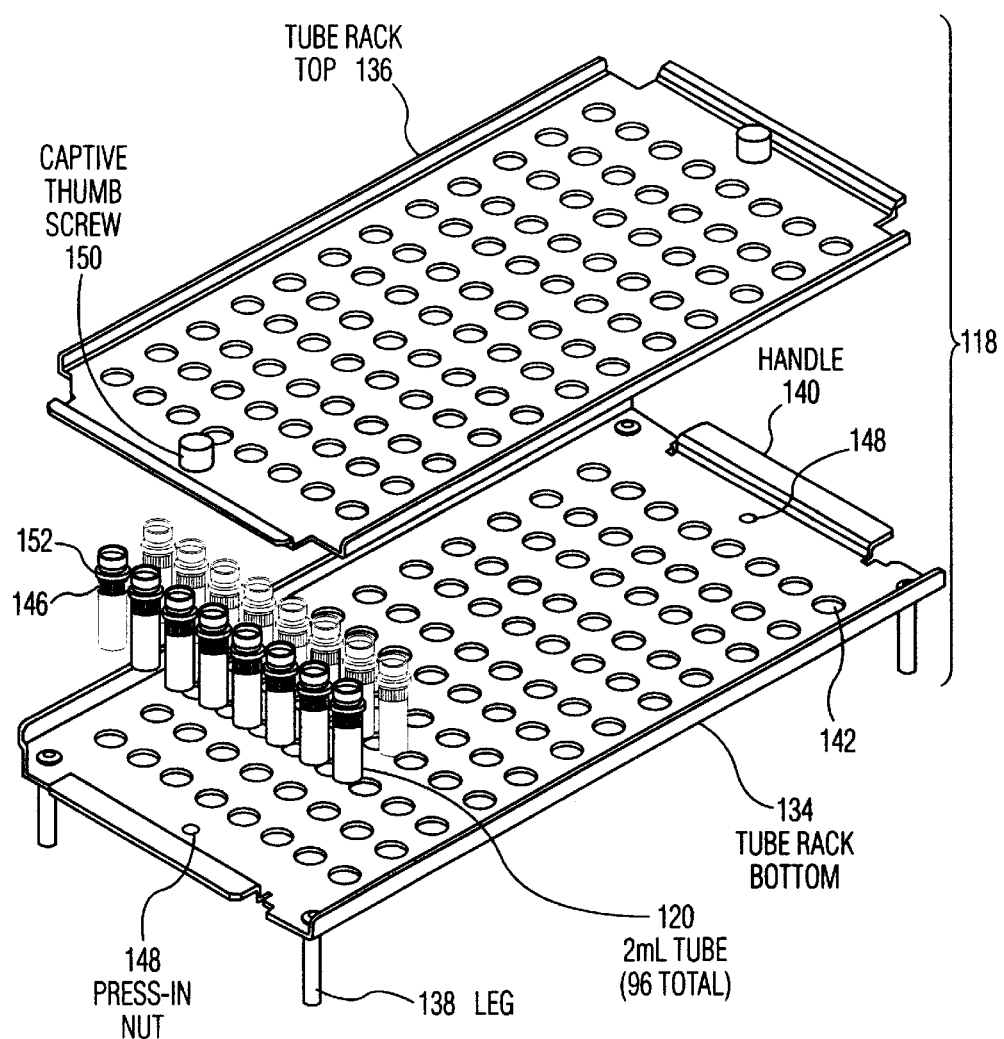
FIG. 4 is a exploded perspective view of an example of a tube rack used with the nucleic acid molecule extractor shown in FIGS. 1–3.
Figure 5:
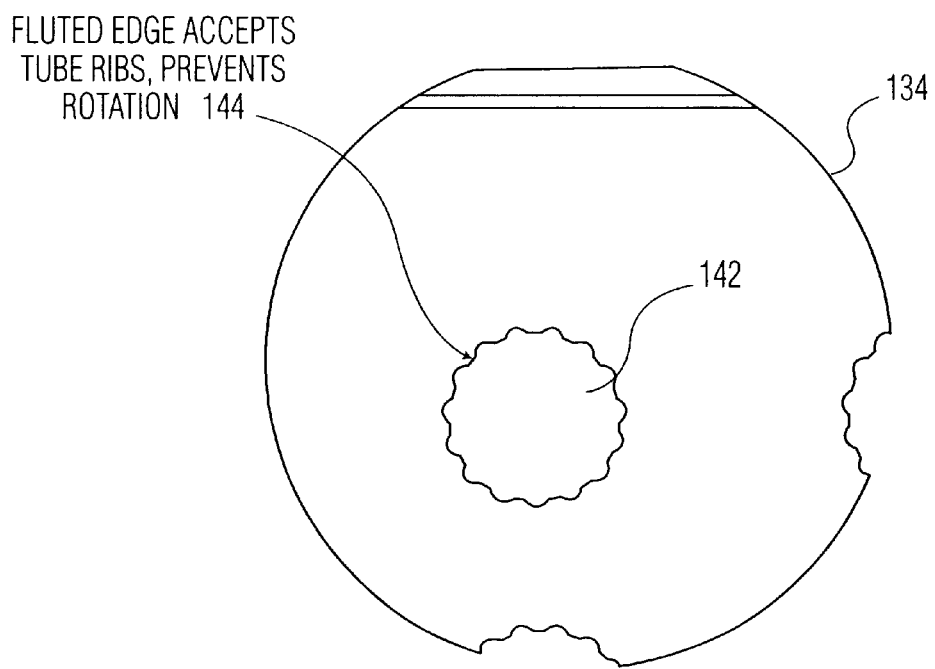
FIG. 5 is a detailed view of an example of the shape of one of the openings in the tube rack shown in FIG. 4.

As discussed above, the extractor 102 includes and is adaptable for use with a rack 118, the details of which are shown with more specificity in FIGS. 4 and 5. In particular, the rack 118 includes a bottom 134 and a top 136. The bottom 134 includes a plurality of legs 138, a handle 140 and a plurality of openings 142 therein. As shown in FIG. 5, the openings 142 include edges 144 which are configured to engage with projections 146 on the exterior of the tubes 120 to prevent the tubes 120 from rotating within the openings 142 when, for example, a cap (not shown) is being screwed onto a top of the tube 120.

As further shown in FIG. 4, the bottom 134 of rack 118 includes two openings, each having a press-in nut 148 inserted therein. Each nut receives the threaded portion of a captive thumb screw 150 which secures the top 136 of the rack 118 to the bottom 134 after the tubes 130 have been inserted into the opening 142. The top 136 abuts against a shoulder 152 which is positioned proximate to the tops of the tubes 120, and thus prevents the tubes 120 from falling out of the rack 118, or being inadvertently lifted out of the rack by the pipette tips discussed above, when the robot 104 is adding or removing solution to and from the tubes 120.

Further details of the extractor 102 are shown in FIGS. 6–9 as will now be described. As illustrated, the extractor 102 includes a plurality of heat sink blocks 154 disposed between the fixed sides 122 and thus, in the interior of the extractor 102. In this example, the extractor includes six heat sink blocks 154. The heat sink blocks are supported by a base plate 156 of the extractor 102 as shown, in particular, in FIG. 6. Each fixed side 122 includes a fixed cam slot 158 which extends in a vertical or substantially vertical direction. The cam slots receive shoulder screws 160 (see FIGS. 2 and 3) which pass through angled cam slots 162 (see FIG. 2) and through respective fixed cam slots 158. In this example, angled cam slots 162 extend at an angle of at or about 45° with respect to the vertical. As described in more detail below, each pair of shoulder screws 160 (two aligned shoulder screws on opposite sides of the extraction 102) are coupled to a respective magnet carrier 164 which can be, for example, a single metal bar, such as an aluminum bar, to which is mounted at least one permanent magnet 166. The magnets 166 can be, for example, neodymium magnets. In this example, the extractor 102 includes seven pairs of shoulder screws 160 and seven corresponding magnet carriers 164 and their respective magnets 166. The shoulder screws 160 are inserted into the respective ends of the magnet carriers 164 as shown. As further illustrated, a nylon sleeve 167 is placed about each shoulder screw 160 and can rotate about the shoulder screw 160 to reduce friction between the shoulder screw 160 and the edges of the fixed sides 122 and cam plates 124 that form the fixed cam slots 158 and angled cam slots 162, respectively. As discussed in more detail below, when the stepper motor 126 which is connected to the motor mount 125 and the cam plates 124, moves the cam plates 124 in a horizontal or substantially horizontal direction with respect to the fixed sides 122, the angled cam slots 162 force the shoulder screws 160 to move in a vertical direction along the fixed fixed cam slots 158 and therefore raise or lower the magnet carriers 164 and their respective magnets 166 for reasons discussed below.

Figure 6:
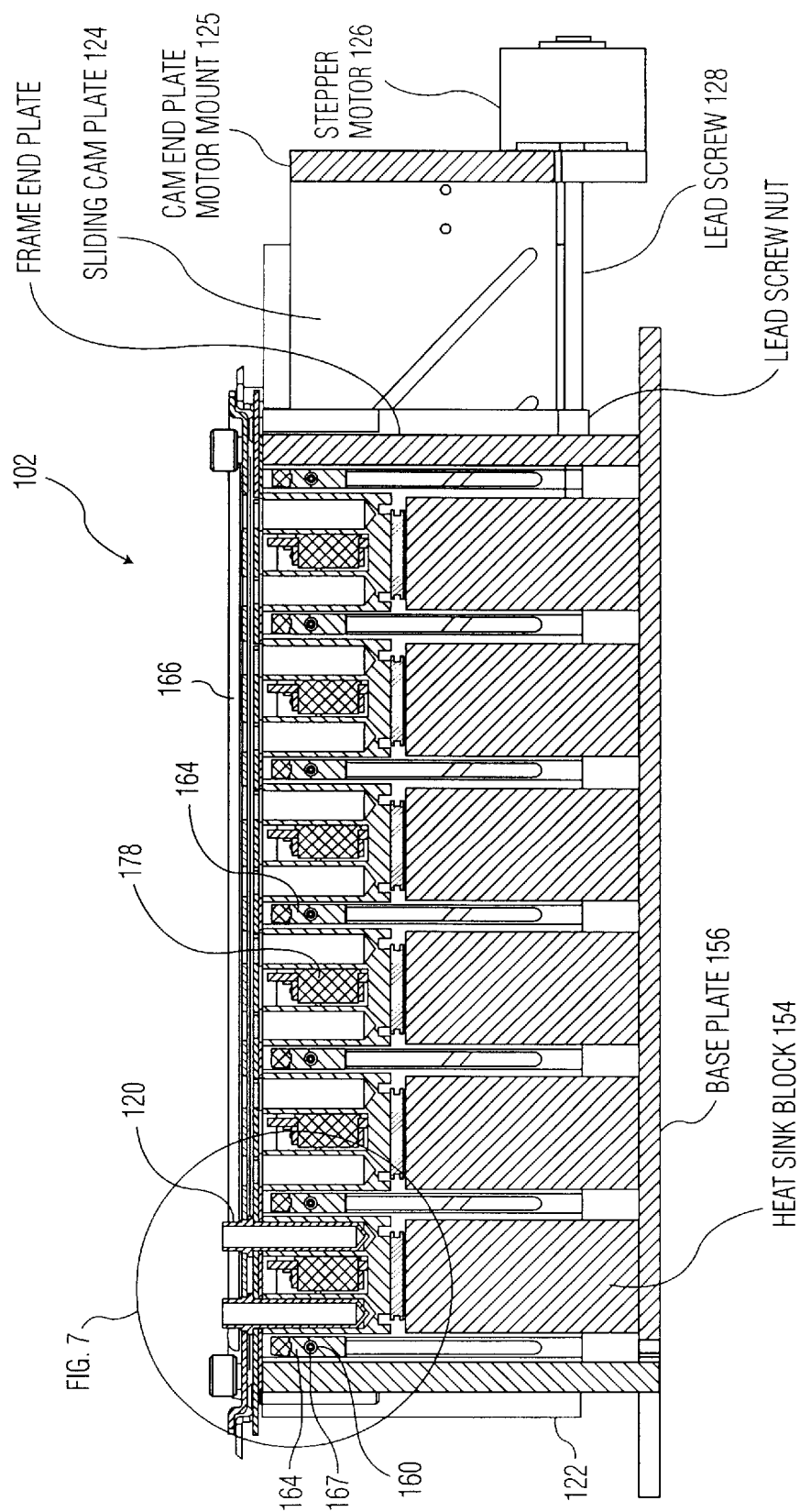
FIG. 6 is a cross-sectional view of the nucleic acid molecule extractor taken along lines 6—6 in FIG. 3.
Figure 7:
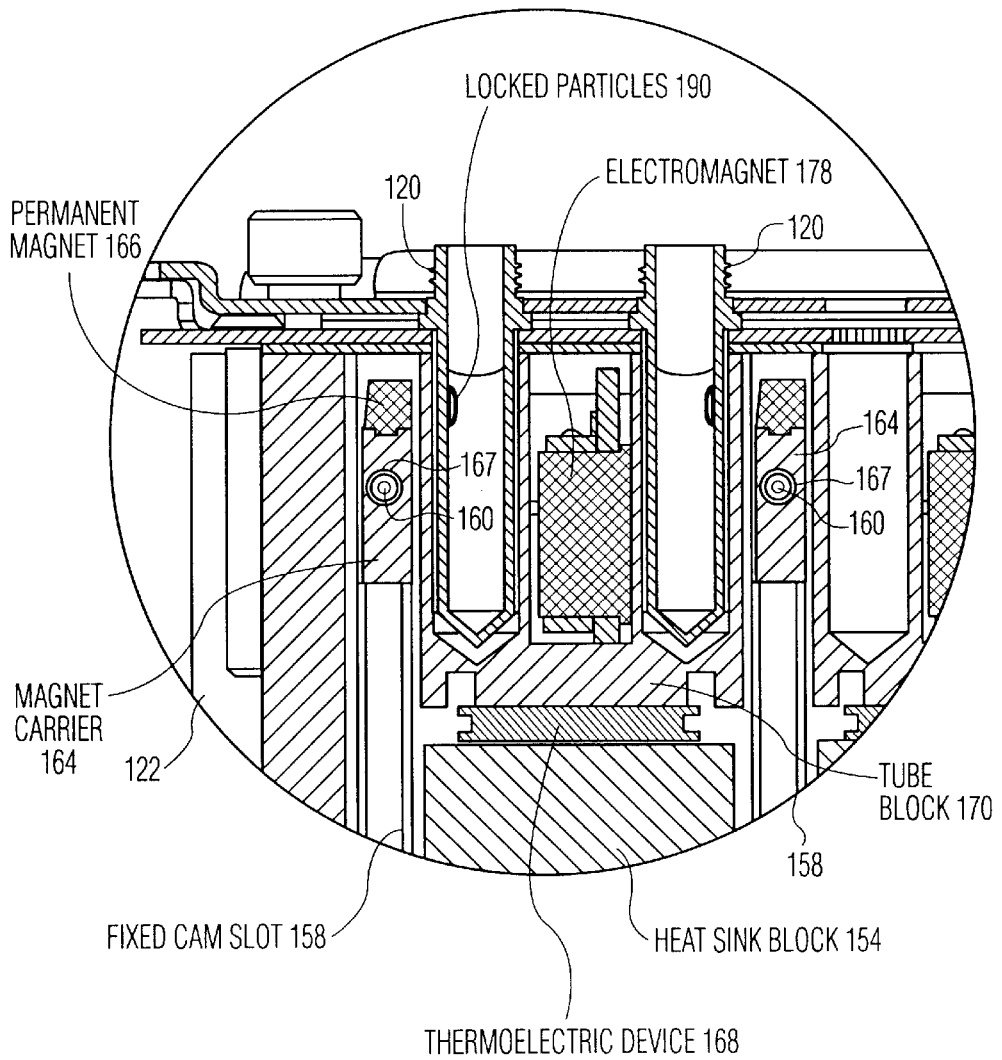
FIG. 7 is a detailed view of the portion of the nucleic acid molecule extractor designated in FIG. 6.

As further illustrated in FIGS. 6 and 7, a thermoelectric device 168 is mounted to the top of each of the respective heat sink blocks 154. A respective tube block 170 is positioned on the top of each of the thermoelectric devices 168 as illustrated.

Figure 8:
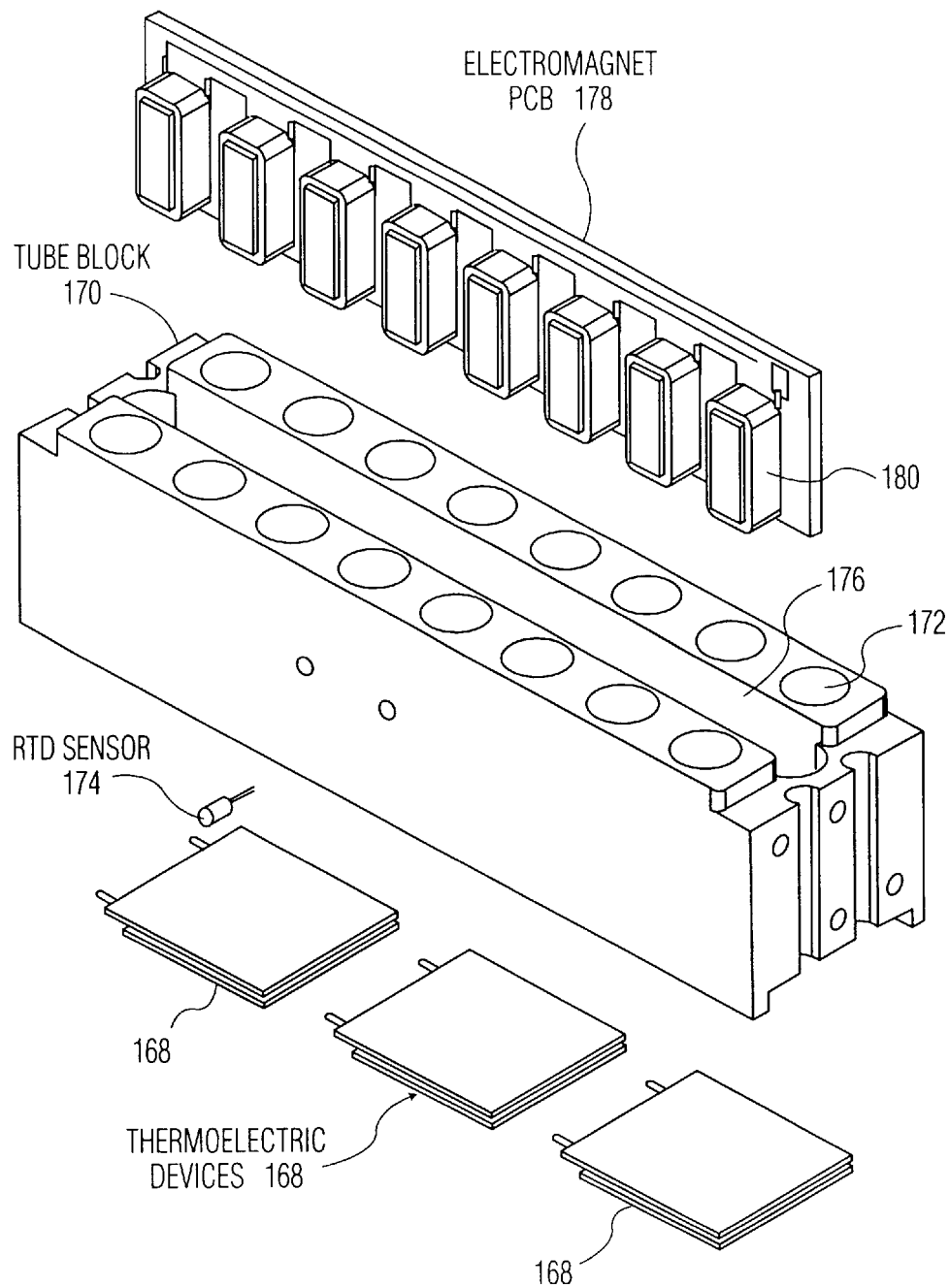
FIG. 8 is a exploded perspective view showing an example of the relationship between the tube blocks, electromagnets and thermoelectric devices included in the nucleic acid molecule extractor shown in FIGS. 1–3, 6 and 7.
Figure 9:
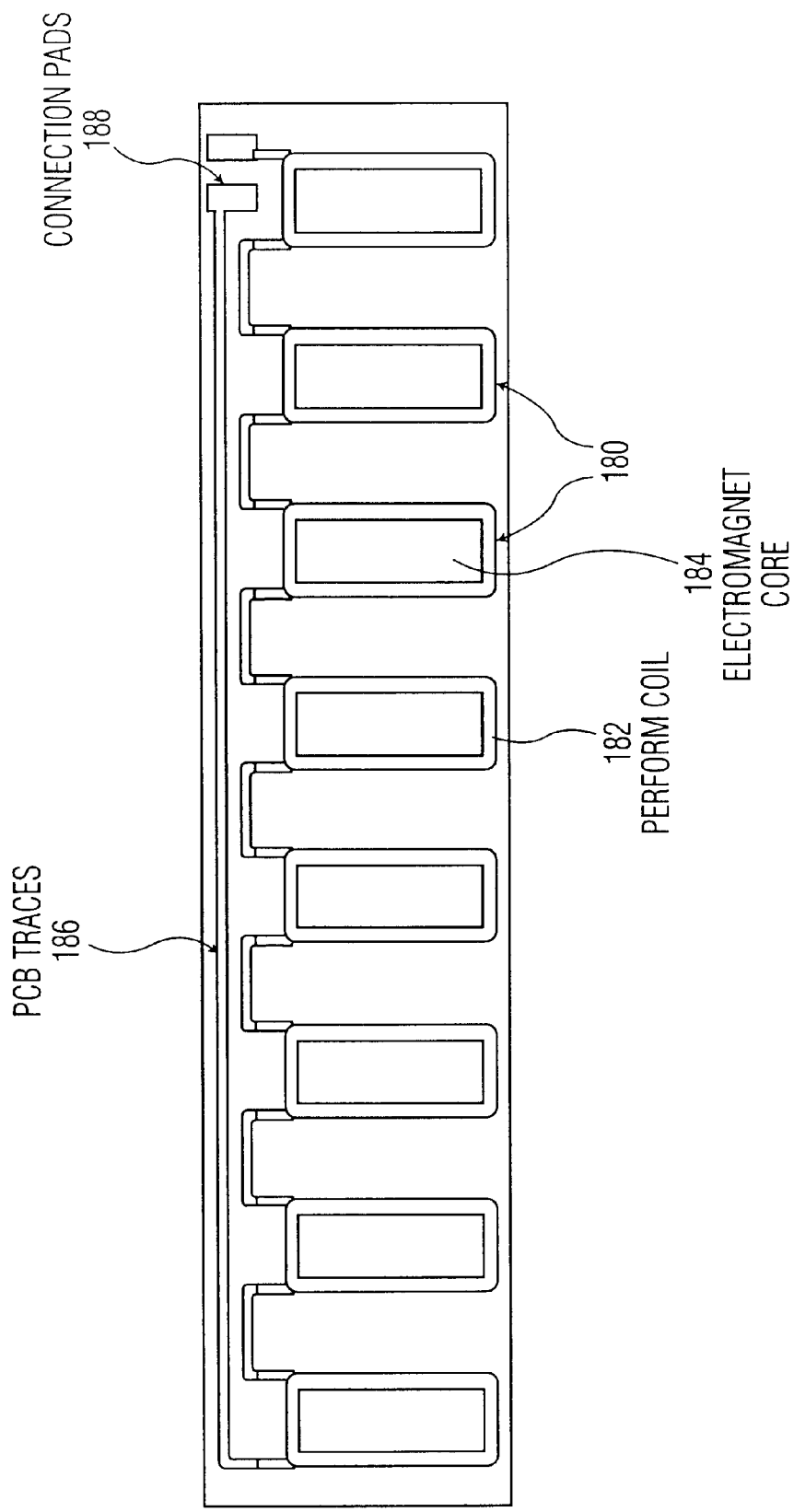
FIG. 9 is a side view of the electromagnet printed circuit board shown in FIG. 8.

As further shown in FIGS. 8 and 9, each respective tube block 170 includes a plurality of openings 172, which are each adapted to receive a respective tube 120. Also, in this example, three thermoelectric devices 168 are associated with each tube block 170 and therefore, three thermoelectric devices are mounted on the top of each respective heat sink block 154. The thermoelectric devices 168 can be controlled to apply heat to tube block 170 or to extract heat from tube 170, as can be appreciated by one skilled in the art, under the control of the controller (not shown). Each tube block 170 also has a resistive temperature device (RTD) sensor 174 for sensing the temperature of the tube block and providing a signal to the controller so that the controller can appropriately control the thermoelectric devices 168.

As further illustrated, each tube block 170 has a slotted opening 176 into which is received an electromagnet circuit board 178 having a plurality of electromagnets 180 mounted thereon. The electromagnets 180 each include a preform coil 182 surrounding an electromagnetic core 184, and are coupled in series to PCB traces 186, which are coupled via connection pads 188 to the controller (not shown). As discussed in more detail below, the controller applies a current to electromagnets 180 which causes the electromagnets to generate an alternating current (AC) magnetic field.

As further shown in FIGS. 6 and 7, the adjacent tube blocks 170 are spaced at a sufficient distance to allow magnet carriers 164 and permanent magnets 166 to slide proximate to the tube openings 172 and therefore proximate to the tubes 120 for purposes discussed in more detail below. In this example, each tube block 170 includes tube rows, each having eight openings 172. The extractor 102 includes six tube blocks 170. Thus, the extractor 102 includes 96 openings 172.

The operation of the extractor 102 with respect to the system 100 will now be described with reference to FIGS. 1–3, 6, 7 and 10–12. Initially, samples containing cells are provided in sample input tubes 112. These samples may be of any type, including biological fluids such as blood, urine and cerebrospinal fluid, tissue homogenates and environmental samples, that are to be assayed for nucleic acids (DNA or RNA) of interest. After the start step 1000, the robot 104 is first controlled in step 1010 to move to the pipette tip racks 108 to pick up a plurality of pipette tips, for example, four pipette tips (not shown). The robot 104 is then controlled to position the pipette tips over a respective number of sample tubes 112 and draw the samples into the respective pipette tips. The robot then moves the pipette tips over to the extractor 102, and releases the samples into respective sample tubes 120 that have been loaded in advance into the rack 118 positioned on the extractor 102.

Each sample tube 120 has been previously supplied with magnetically responsive particles. Although any type of magnetically responsive particle may be used, including particles having polymeric coatings, the particles disclosed in U.S. Pat. No. 5,973,138 referenced above are preferred. Each of the sample tubes 112 also has lyse solution which lyses the cell samples.

The above process continues until all of the samples from the sample input tubes 112 have been inserted into the corresponding tubes 120 in the extractor 102. It is noted that the number of samples drawn at each time (i.e., four samples in this example) can vary as desired. It is also noted that each time the robot draws its samples from sample tubes 112 into pipette tips and then dispenses those samples into corresponding tubes 120, the robot moves to a discard position to discard the pipette tips. The robot 104 then selects four new pipette tips to transfer four new samples from the input tubes 112 to the tubes 120.

Once all of the samples have been loaded into the respective sample tubes 120, the controller controls the thermoelectric devices 168 in step 1020 to apply heat to the solutions in the tubes 120 to lyse the samples. In this example, the solutions in the tubes 120 are heated to a temperature at or about 70° C. Once the lysing has been completed, the controller controls the thermoelectric device 168 to extract heat from the tube blocks 170, the sampling tubes 120 and the solutions contained therein, to cool the solutions to substantially room temperature.

Once the lysing and cooling processes are completed, the robot 104 is controlled in step 1030 to transfer a suitable acidic solution, such as that described in U.S. Pat. No. 5,973,138, into the sample tubes 120. To do this, the robot 104 moves back and forth between the pipette tip racks 108, the bulk reagent containers 114, extractor 102, and the pipette disposal section (not shown) to transfer the acidic solution to, for example, four tubes 120 at a time. The robot 104 transfers acidic solution to four corresponding tubes 120. At this time, the controller controls the electromagnets 178 to generate an AC magnetic field, which demagnetizes (degausses) the particles 190 so that the particles can freely mix with the acidic solution. In this example, the AC magnetic field is applied at a rate of at or about 60 times per second. The robot 104 then mixes the solution in the tubes 120 by drawing the solution into the pipette tips and discharging the solution back into the tubes 120 in a controlled manner, while raising and lowering the pipette tips into and out of the tubes 120 in a controlled manner to maintain minimum tip submersion.

Once the robot 104 has transferred acidic solution to four corresponding tubes 120 and has performed the mixing operations, the controller turns off the electromagnets to remove the AC magnetic field. The acidic solution that has been added to the cell sampling tube 120 causes the nucleic acid molecules to become bound to the magnetically responsive particles 190. Once the acidic solutions have been added to the samples in the sample tubes 120, the controller controls the stepper motor 126 in step 1040 to move the cam plates 124 in a direction indicated by arrow A in FIG. 10. This drives the shoulder screw 160 in an upward direction along fixed cam slots 158 so that the magnets 164 are positioned proximate to the tubes 120. Therefore, the molecule-bound particles 190 are attracted by the magnets 164 and become adherent to the sides of the tubes 120 as shown, for example, in FIG. 7.

The robot 104 is then controlled in step 1050 to use the pipette tips to remove the solution from the tubes 120 and discard the solution in a waste container (not shown). As in the operations discussed above, each time the robot 104 uses pipette tips to remove solution from respective tubes 120, the robot 104 discards the pipette tips and uses new pipette tips before repeating the process on the remaining tubes 120.

The robot 104 is then controlled in step 1060 to add a washing solution to each of the tubes 120. When the wash solution is being added to the tubes 120, the controller controls the cam plates 124 to move in the direction indicated by arrow B in FIGS. 11 and 12, which causes the shoulder screws 160 to drive the magnet carriers 164 and, hence the permanent magnets 166, in a downward direction in their respective fixed cam slots 158. When the magnets 166 are moved away from the tubes 120, the particles 190 are allowed to fall back into the bottoms of the tubes 120. At this time, the controller controls the electromagnets 178 in step 1070 to generate an AC magnetic field, which demagnetizes the particles 190 so that the particles can freely mix with the wash solution being added to the tubes 120. A rapid sequence of several aspirate and dispense cycles (e.g., 5 to 30 cycles, or any suitable number) is used to perform the mix the particles with the wash solution. Once the robot 104 has completed mixing the wash solution, the controller turns off the electromagnets to remove the AC magnetic field.

Figure 10:
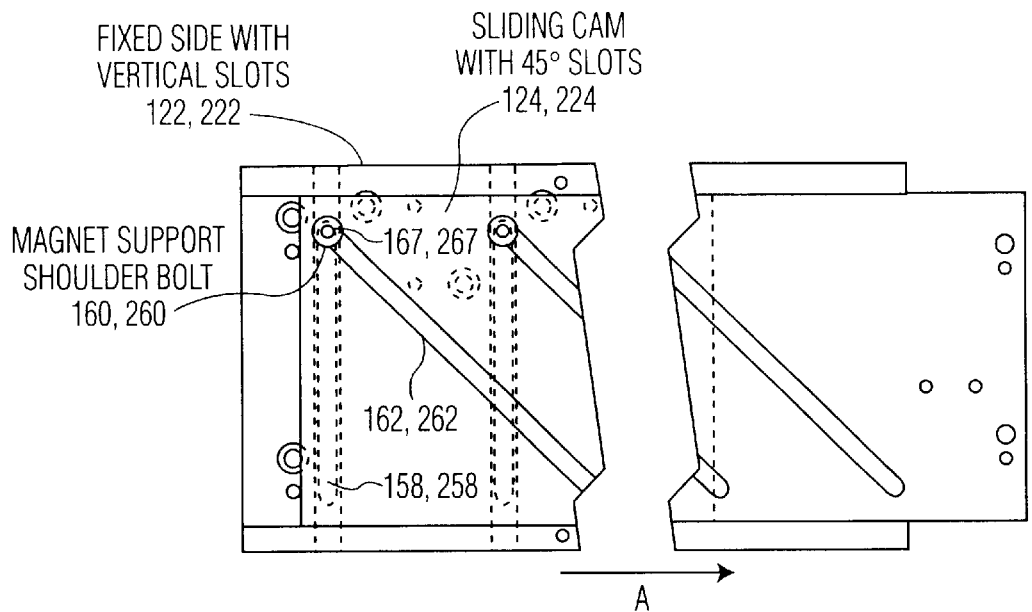
FIG. 10 is diagrammatic view illustrating the relationship of the fixed side and sliding cam of the nucleic acid molecule extractor shown in FIGS. 1–3, 6 and 7 when the movable magnets are positioned as shown in FIGS. 6 and 7.
Figure 11:
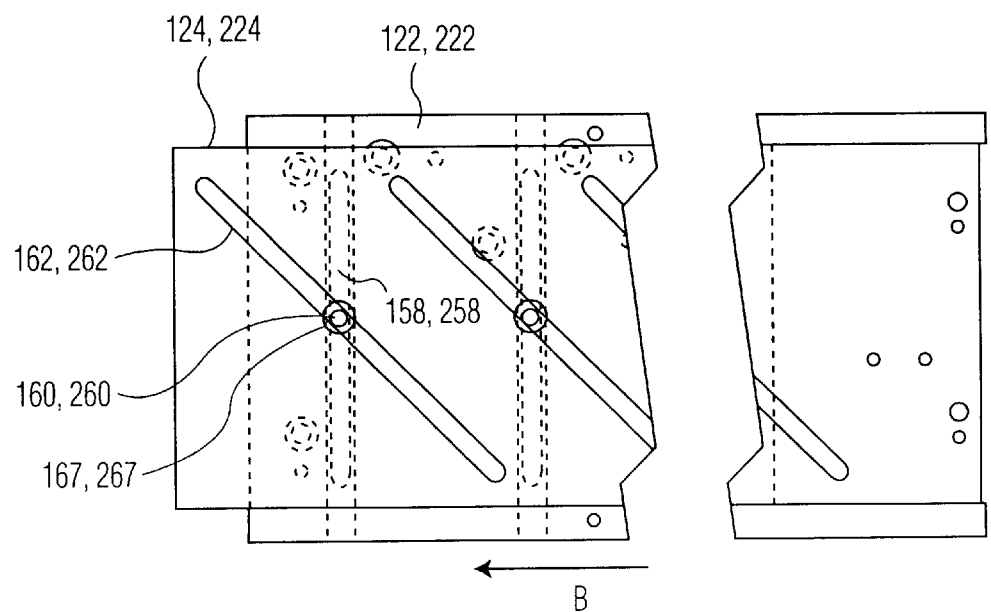
FIG. 11 is a diagrammatic view illustrating the relationship between the fixed side and sliding cam of the nucleic acid molecule extractor shown in FIGS. 1–3, 6 and 7 when the magnets are being moved in a downward direction away from the tubes.
Figure 12:
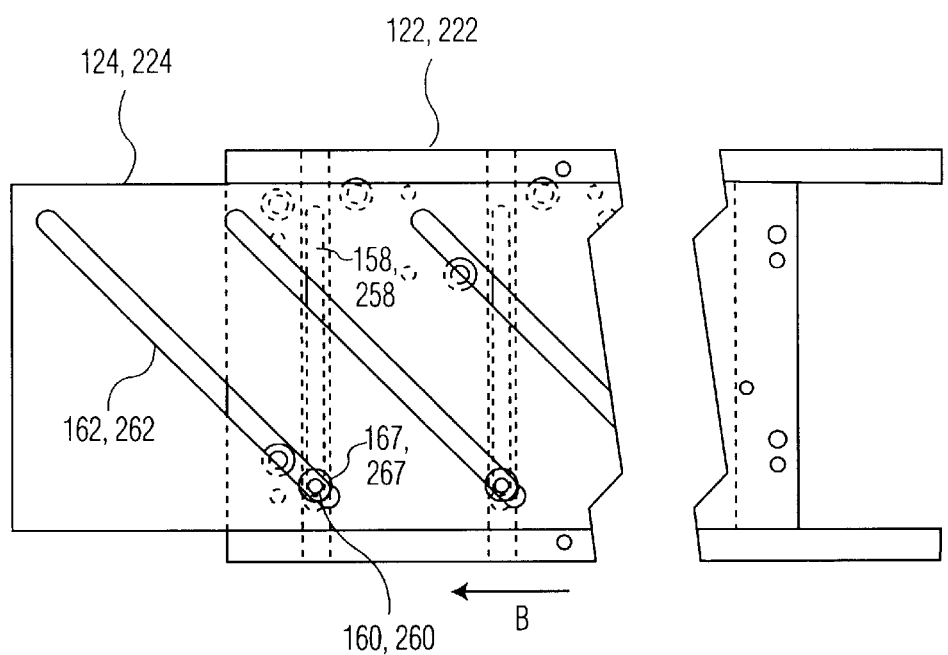
FIG. 12 is a diagrammatic view illustrating the relationship between the fixed side and sliding cam of the nucleic acid module extractor shown in FIGS. 1–3, 6 and 7 when the movable magnets are positioned at the downward most position away from the tubes.
Figure 13:
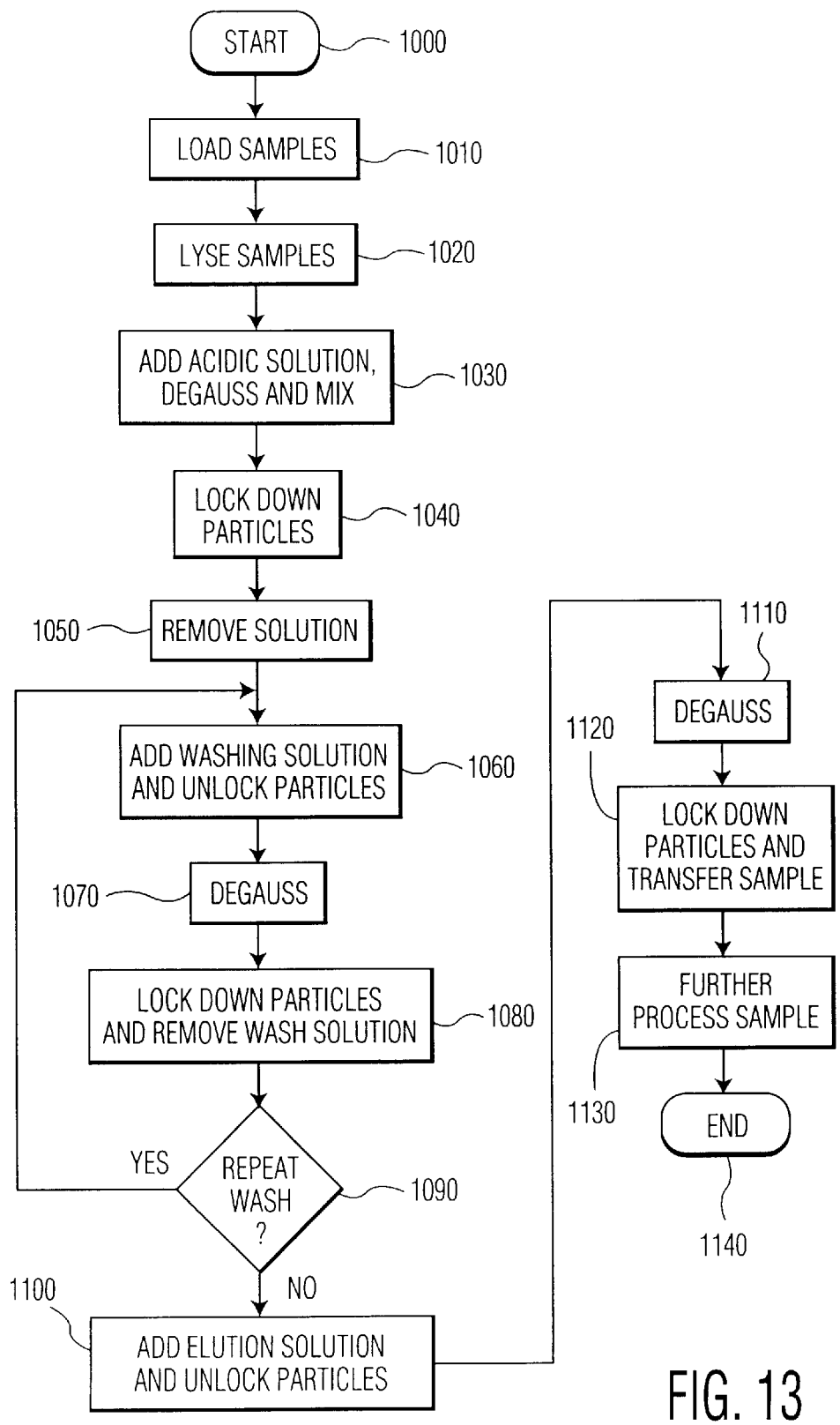
FIG. 13 is a flowchart illustrating an example of the sequence of operations performed by the preparation system and, in particular, the extractor shown in FIGS. 1–3, 6 and 7.
Figure 14:
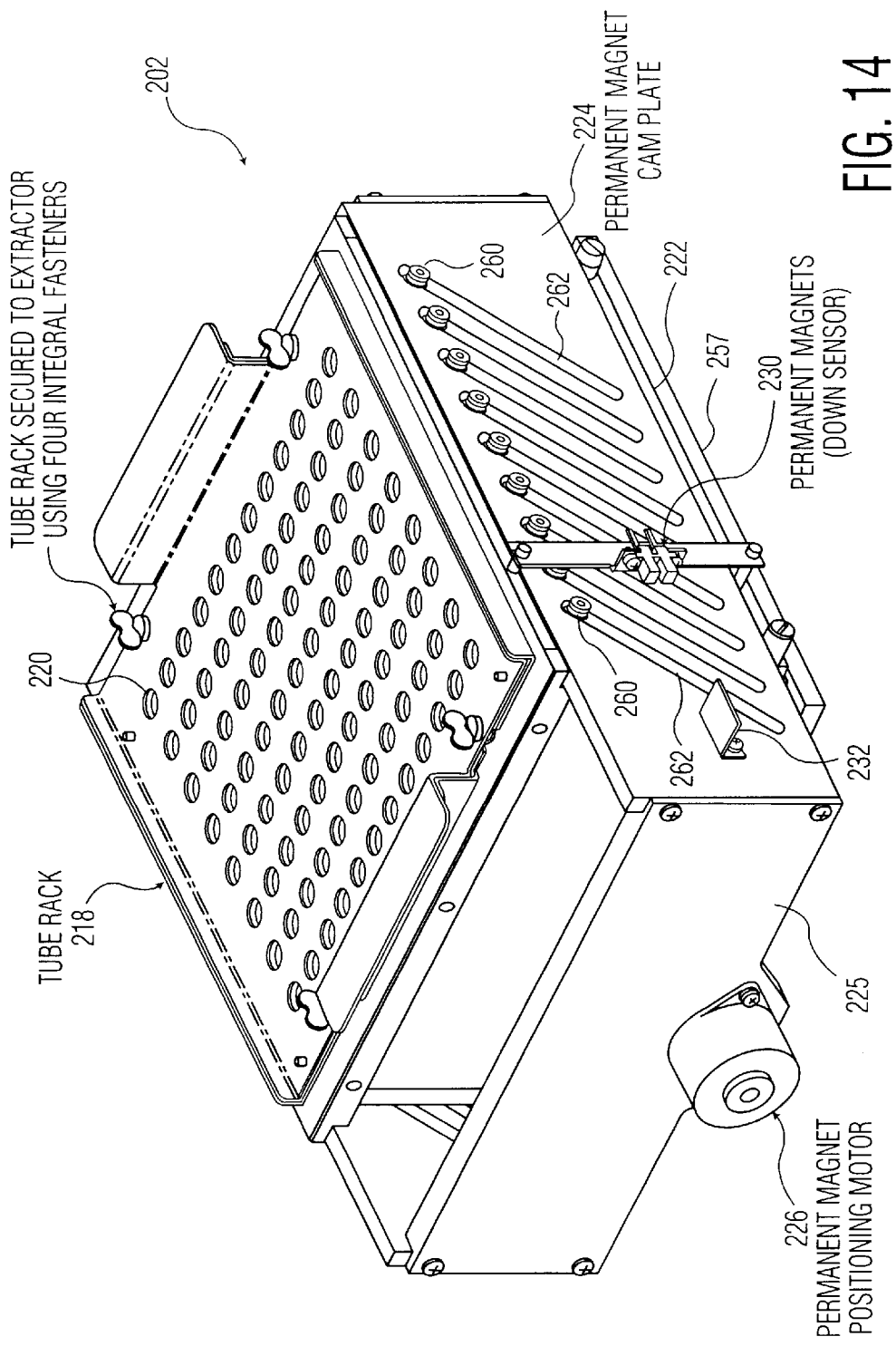
FIG. 14 is a perspective view of another example of the nucleic acid molecule extractor shown in FIG. 1.
Figure 15:
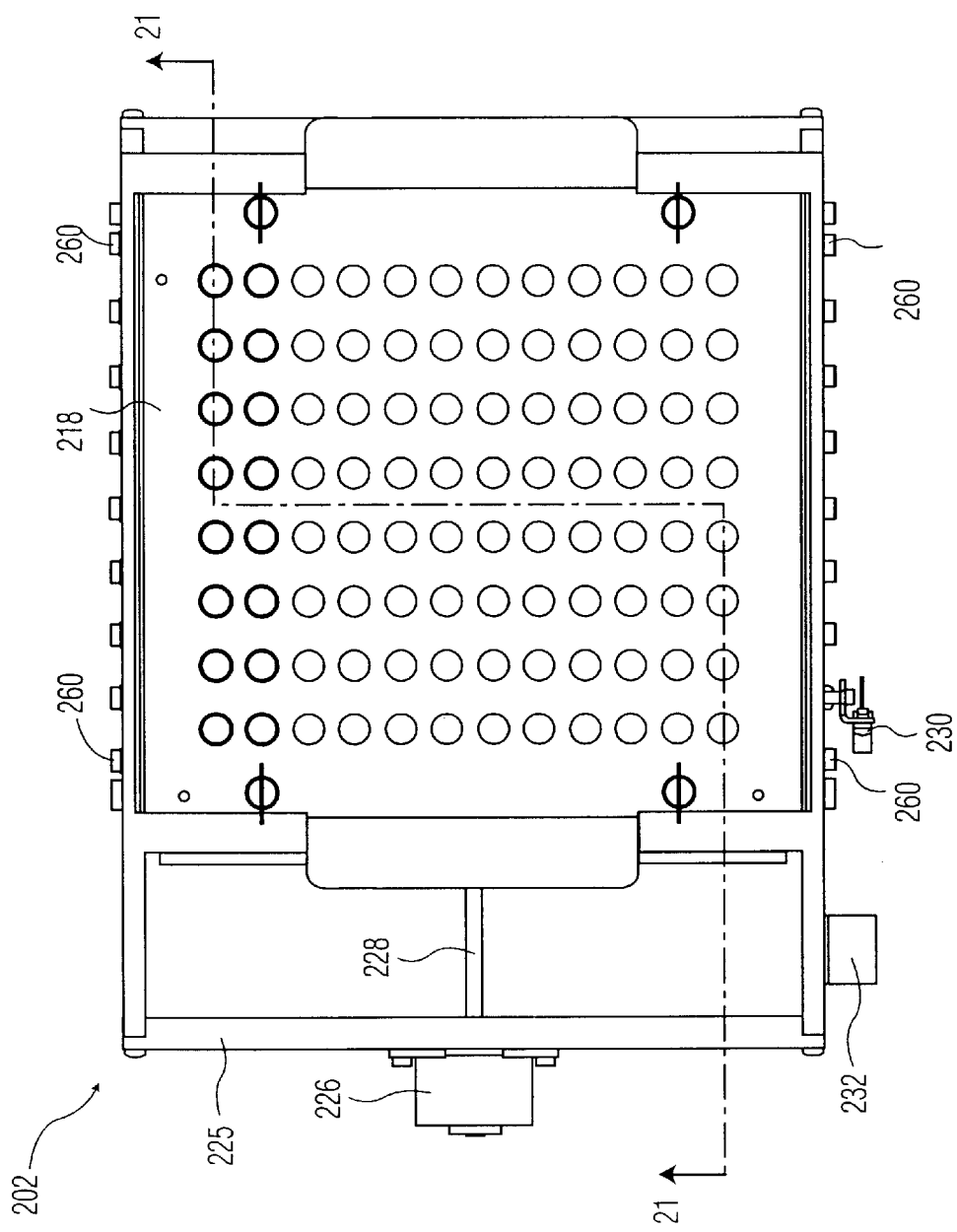
FIG. 15 is a top view of the nucleic acid molecule extractor shown in FIG. 2.

After the wash solution has been added and mixed with the particles, the controller controls the stepper motor 126 in step 1080 to move the cam plates 124 in the direction along arrow A shown in FIG. 10, to drive the magnets 166 in the upward direction to be proximate to the tubes 120. The magnets 166 thus secure the molecule-bound particles 190 to the sides of the tube again as shown in FIG. 7. The robot 104 is then controlled to use the pipette tips (not shown) to remove the wash solution from the tubes 120. This wash step may be repeated as many times as necessary to wash the particles, e.g., two times, as decided in step 1090.

The robot 104 is then controlled in step 1100 to add an elution reagent, such as those described in U.S. Pat. No. 5,973,138 referenced above, to the tubes 120. During this time, the controller controls the cam plates 124 to move in the direction indicated by arrow B in FIGS. 11 and 12, which causes the shoulder screws 160 to drive the magnet carriers 164 and, hence the permanent magnets 166, in a downward direction in their respective fixed cam slots 158. When the magnets 166 are moved away from the tubes 120, the particles 190 are allowed to fall back into the bottoms of the tubes 120 into the elution solution. The elution solution causes the molecules to become unbound from the particles 190. Also, the controller can controls the electromagnets 178 to generate an AC magnetic field, which demagnetizes the particles 190 so that the particles can freely mix with the elution solution being added to the tubes 120. In a manner similar to that described above, the robot 104 uses new pipette tips for each group of tubes 120 to which the elution solution is being added from the bulk reagent tank 114.

After the elution solution has been added to and mixed within all of the tubes 120, the stepper motor 126 is controlled in step 1120 to move the cam plates 124 along direction A, as shown in FIG. 10, to move the magnets 166 proximate to the tubes 120. The robot 104 is then controlled to use the pipette tips to transfer the elution solution containing the nucleic acid molecules that have been released from the particles 190 into the microtiter trays 116. As with the operations described, the robot 104 uses fresh groups of pipette tips to transfer each group of sample to the respective priming wells and the microtiter trays 116. Once all the samples have been transferred to the priming wells, the robot 104 uses fresh groups of pipette tips to transfer the samples to the amplification wells and microtiter trays (not shown). Once all the samples have been transferred into the amplification wells, the microtiter trays can be placed in a suitable reading device, such as the BDProbeTec™ ET system described above, and the process is completed in step 1140. In an alternative embodiment, the robot can transfer the samples directly from the priming wells to the amplification stage of the BDProbeTec™ ET system eliminating the need to move or convey microtiter trays.

Another embodiment of the extractor will now be described with regard to FIGS. 14–22. The extractor 202 shown in these figures includes a removable rack 218, which is similar to rack 118 discussed above in that it can receive a plurality of tubes 220 containing magnetically responsive particles such as those described above. In this example, each tube 120 has a 2 mL capacity and contains a dried down slurry of iron oxide particles and potassium hydroxide.

The extractor 202 further includes fixed sides 222 and cam plates 224 which extend parallel or substantially parallel to fixed sides 222 as shown. The extractor further includes a stepper motor 226 connected to a lead screw 228 which is controlled by a controller (not shown) of the system 100 to slide the cam plates 224 with respect to the fixed sides 222 in a manner similar to cam plates 124 as discussed above. Like extractor 102, extractor 202 includes a home sensor (permanent magnet down sensor) 230 that is connected to the controller (not shown). The home sensor 230 detects the home flag 232 to indicate to the controller that the cam plates 224 are positioned with respect to the fixed sides 222 so that the permanent magnets 266 (see FIGS. 21 and 22) are in the down position.

As discussed above, the extractor 202 includes and is adaptable for use with rack 218, the details of which are shown with more specificity in FIGS. 16–19. In particular, the rack 218 includes a bottom 234 and a top 236. The bottom 234 includes a plurality of legs 238, handles 240 and a plurality of openings 242 therein.

Figure 16:
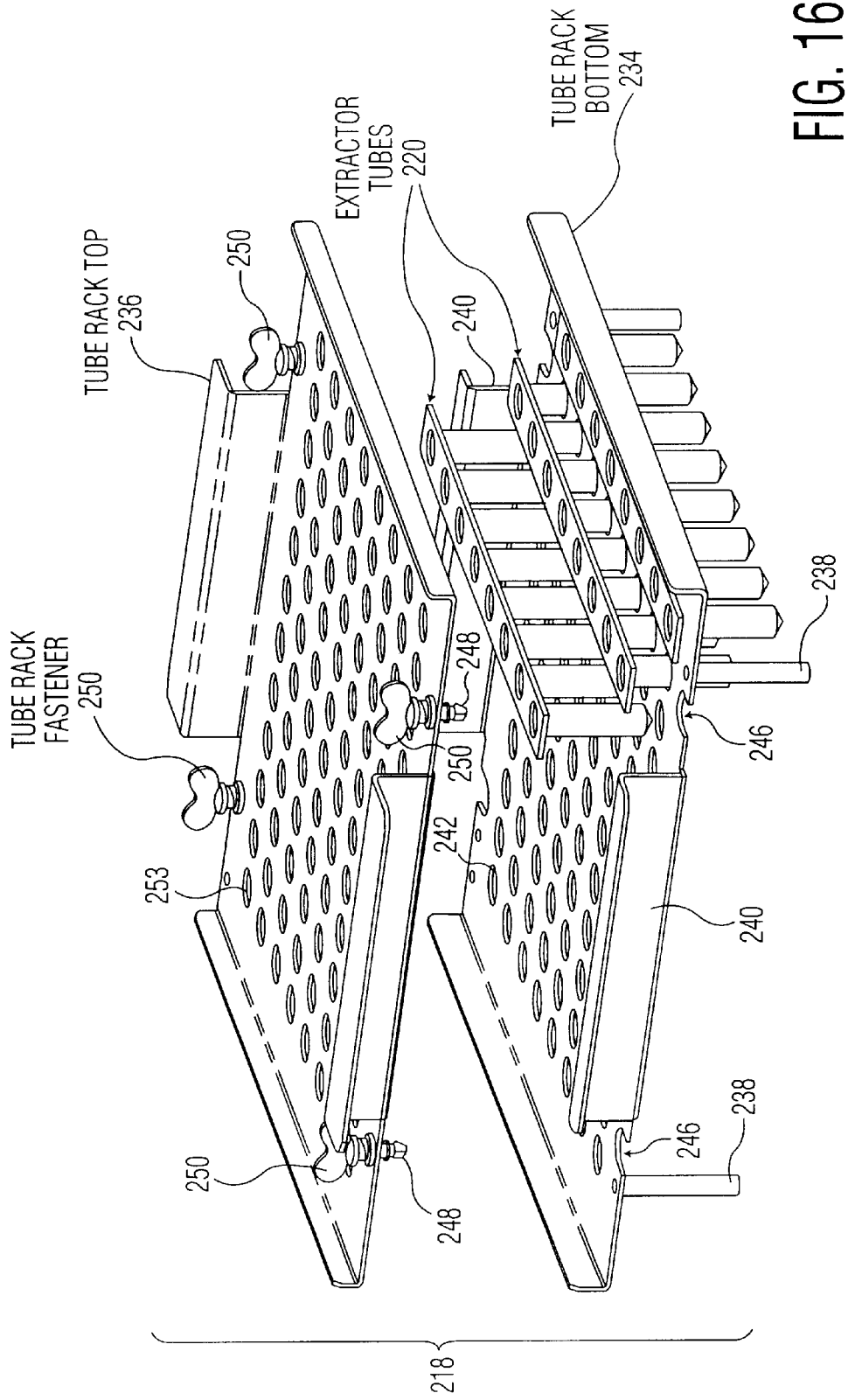
FIG. 16 is a exploded perspective view of an example of a tube rack used with the nucleic acid molecule extractor shown in FIGS. 14 and 15.
Figure 17:
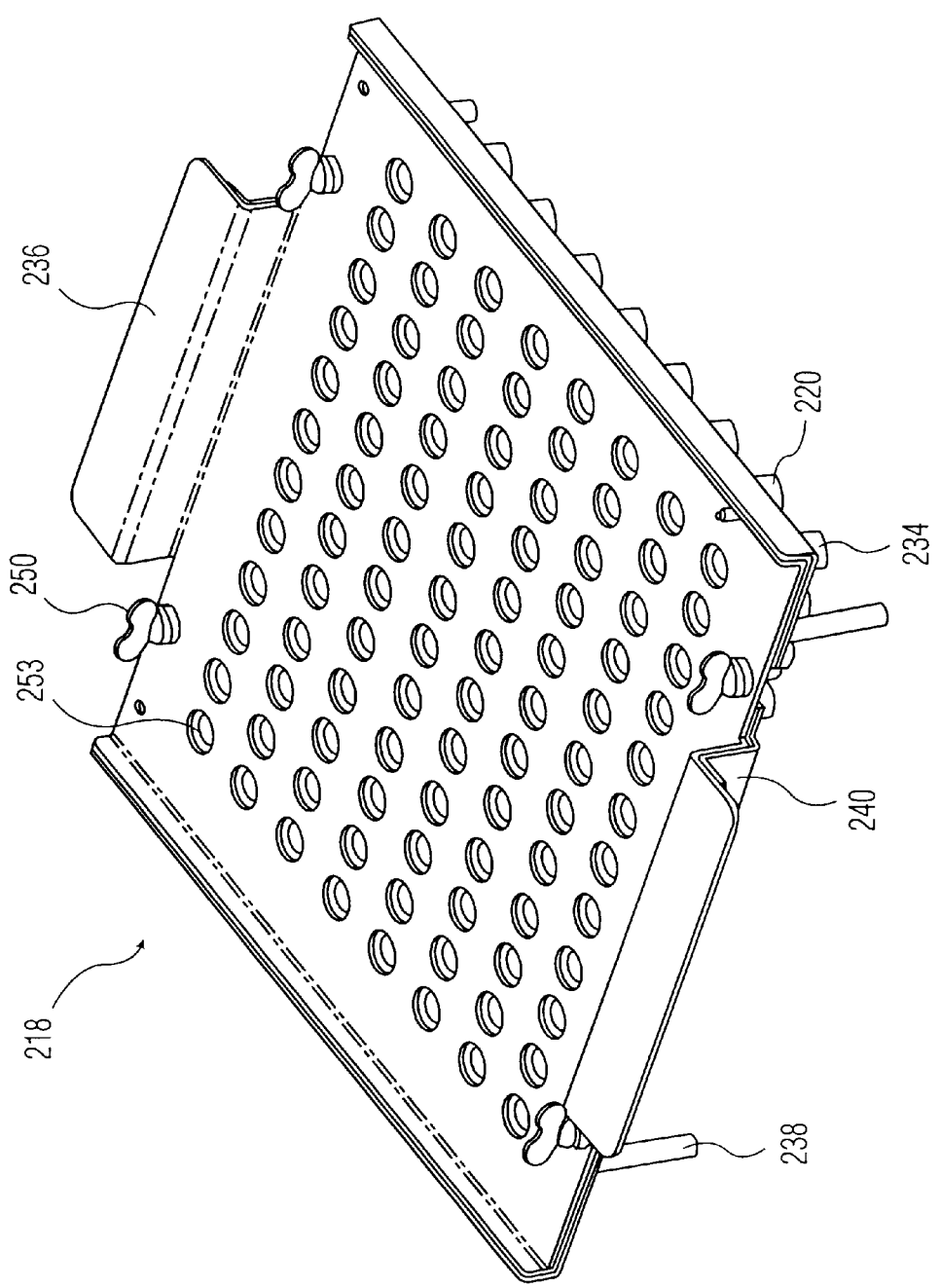
FIG. 17 is a perspective view of an assembled tube rack shown in FIG. 16.
Figure 18:
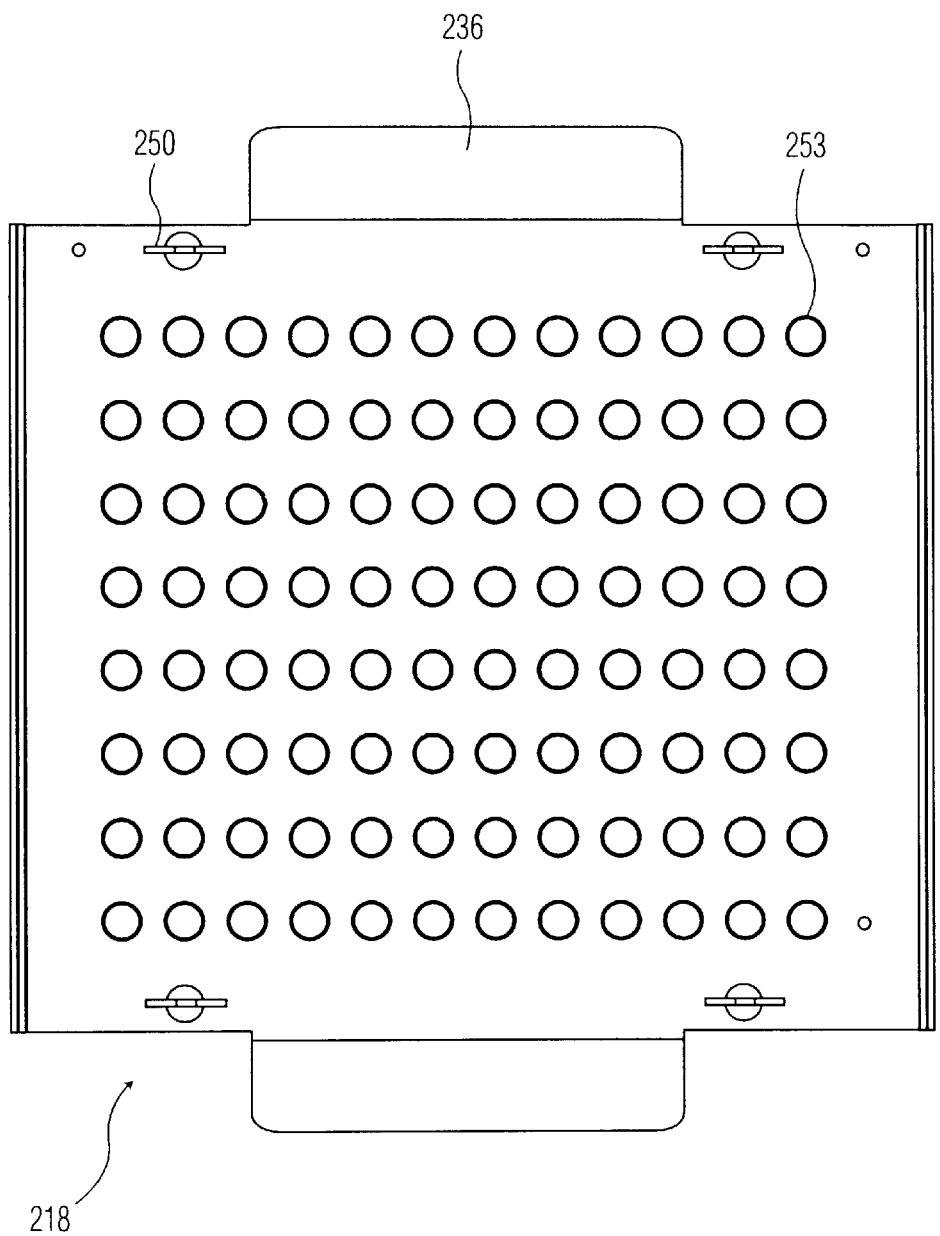
FIG. 18 is a top view of the tube rack as shown in FIGS. 16 and 17.
Figure 19:
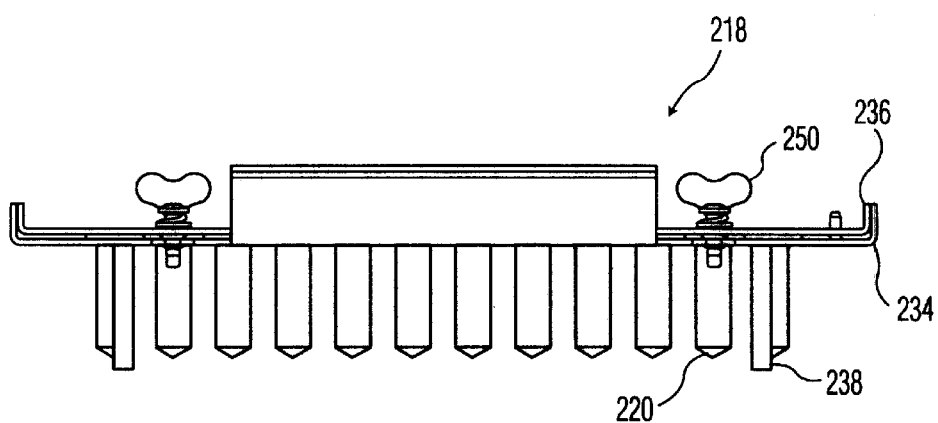
FIG. 19 is a side view of the tube rack as shown in FIGS. 16 and 17.
Figure 20:
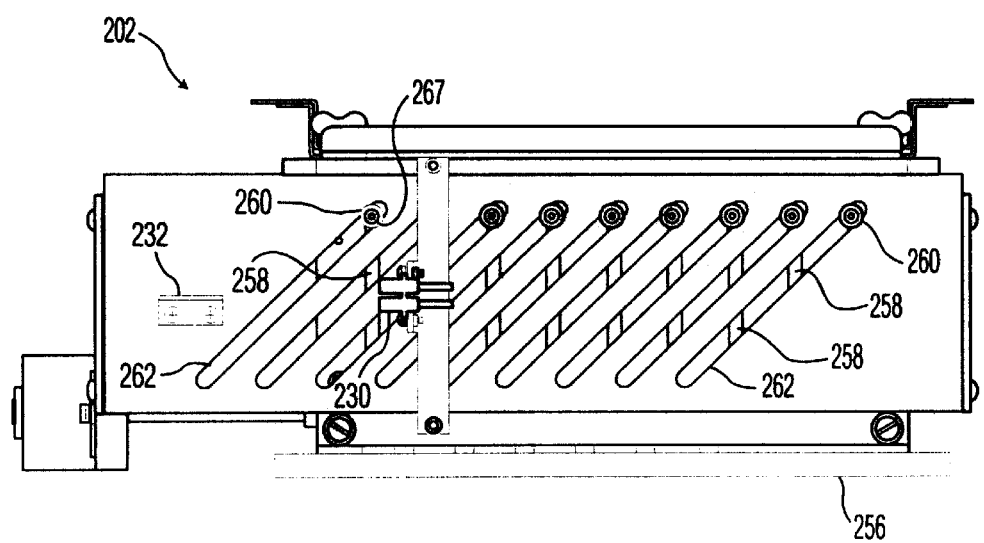
FIG. 20 is a side view of the extractor shown in FIGS. 14 and 15.

As further shown in FIG. 16, the bottom 234 of rack 218 includes four slots 246 therein (two of which are not shown). Each nut receives an engagement portion 248 of a respective tube rack fastener 250 which secures the top 236 of the rack 218 to the bottom 234 after the tubes 230 have been inserted into the openings 242. The top 236 abuts against the tops 252 of the tubes 220, and thus prevents the tubes 220 from falling out of the rack 218, or being inadvertently lifted out of the rack by the pipette tips discussed above, when the robot 104 is adding or removing solution to and from the tubes 220. The top 236 also includes openings 253 which provide access to the tubes 220.

Figure 21:
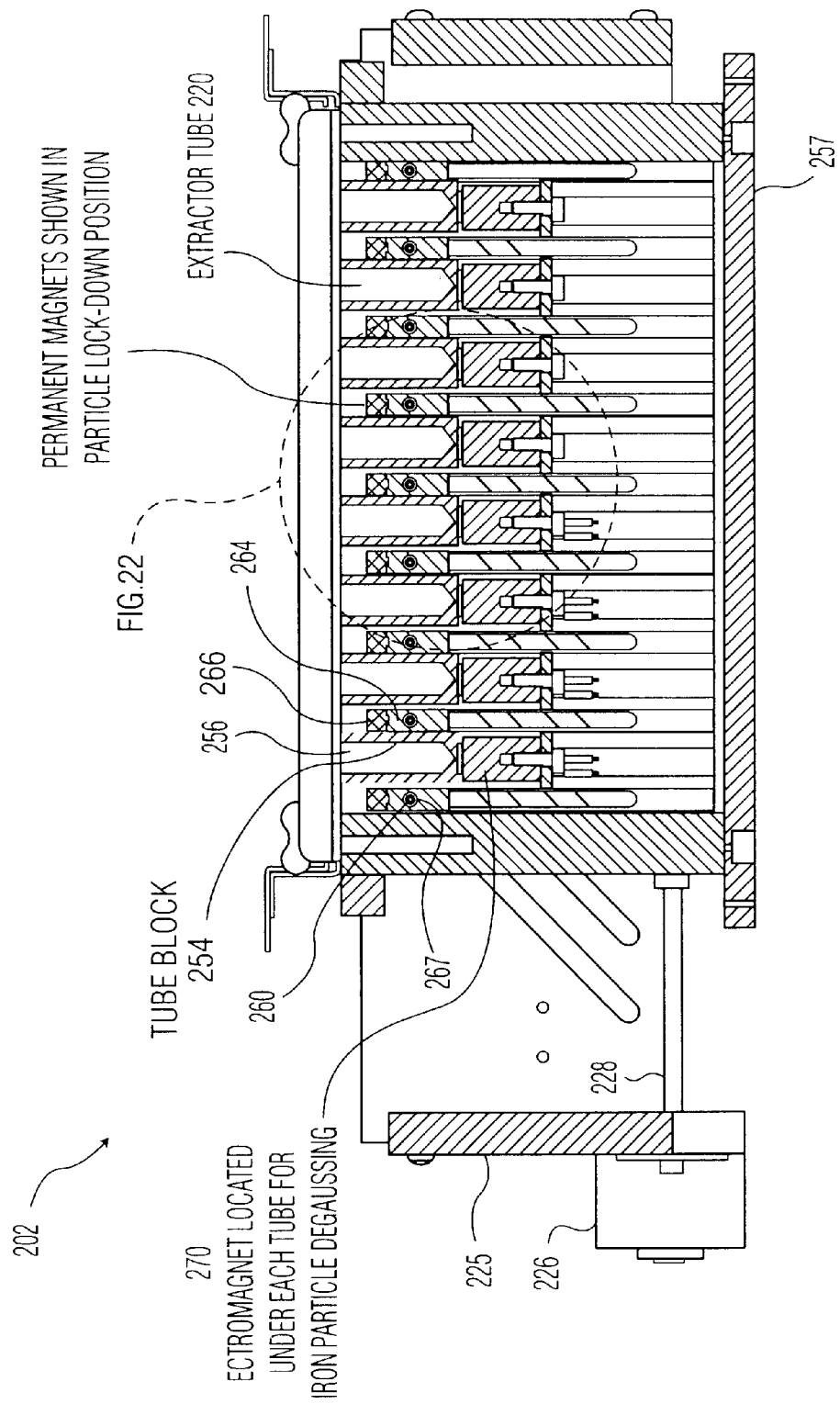
FIG. 21 is a cross-sectional view of the nucleic acid molecule extractor taken along lines 21—21 in FIG. 15.
Figure 22:
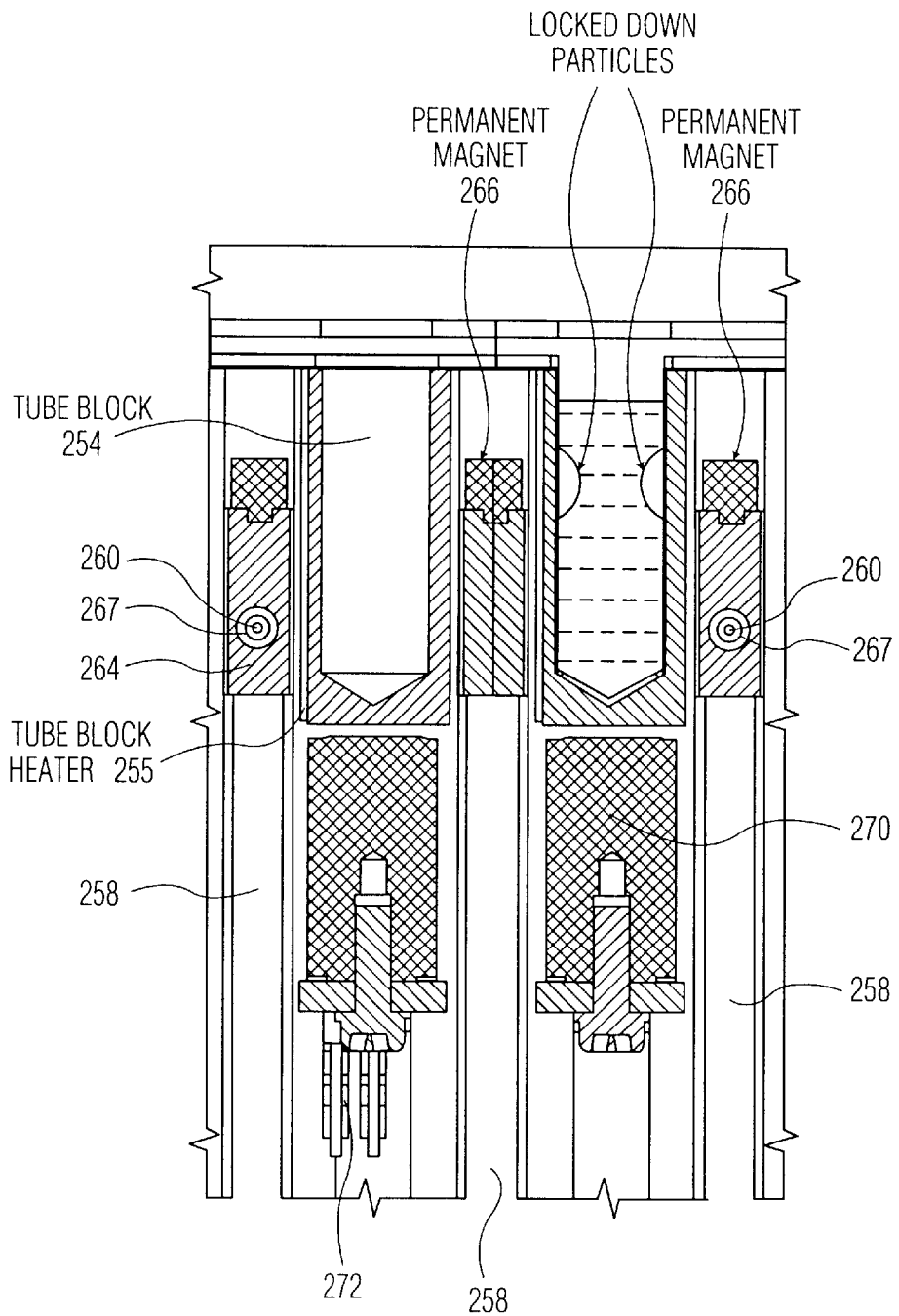
FIG. 22 is a detailed view of the portion of the nucleic acid molecule extractor designated in FIG. 21.

Further details of the extractor 202 will now be described. As illustrated in FIGS. 21 and 22, the extractor 202 includes a plurality of tube blocks 254 disposed between the fixed sides 222 and thus, in the interior of the extractor 202. In this example, the extractor includes eight tube blocks 254 corresponding to the eight rows of tubes. A resistive heating device 255 similar to thermoelectric device 168 discussed above, but which only heats and does not cool, is coupled to each tube block 254 to heat its respective tube block 254 to perform the lysing operation as discussed above. However, if desired, resistive heating device 255 can alternatively be configured as a thermoelectric device similar to thermoelectric device 168 that is capable of heating and cooling. Each tube block 254 also includes a plurality of tube openings 256 for receiving the tubes 220. Furthermore, each tube block 254 includes an RTD that provide temperature readings to the controller (not shown) so that the controller can control the resistive heating devices 255 as necessary to maintain the appropriate temperature.

Each fixed side 222 is supported by a base plate 257 and includes a cam slot 258 (see FIGS. 20 and 22) which extends in a vertical or substantially vertical direction. The cam slots receive shoulder screws 260 which pass through cam slots 262 and to respective cam slots 258. In this example, cam slots 262 extend at an angle of at or about 45° with respect to the vertical. As described in more detail below, each pair of shoulder screws 260 (two aligned shoulder screws 260 being provided on opposite sides of the extractor 202) are coupled to a respective magnet carrier 264 which can be, for example, a single metal bar, such as an aluminum bar to which is mounted at least one permanent magnet 266. The magnets 266 can be, for example, neodymium magnets. In this example, the extractor 202 includes nine pairs of shoulder screws 260 and nine corresponding magnet carriers 264 and their respective magnets 266. The shoulder screws 260 are inserted into the respective ends of the magnet carriers 264 as shown. As further illustrated, a nylon sleeve 267 is placed about each shoulder screw 260 and can rotate about the shoulder screw 260 to reduce friction between the shoulder screw 260 and the edges of the fixed sides 222 and cam plates 224 that form the cam slots 258 and cam slots 262, respectively. In a manner similar to that discussed above with regard to extractor 102, when the stepper motor 226 which is connected to the motor mount 225 and the cam plates 224, moves the cam plates 224 in a horizontal or substantially horizontal direction with respect to the fixed sides 222, the cam slots 262 force the shoulder screws 260 to move in a vertical direction along the fixed cam slots 258 and therefore raise or lower the magnet carriers 264 and their respective magnets 266 for reasons discussed above.

As further illustrated, an electromagnet circuit board 268 having a plurality of electromagnets 270 mounted thereon is positioned below each tube block 254. The electromagnets 270 each include connections 272 which couple to the controller (not shown). As discussed above with regard to electromagnets 178, the controller applies a current to electromagnets 270 which causes the electromagnets to generate an alternating current (AC) magnetic field.

As further shown, the adjacent tube blocks 254 are spaced at a sufficient distance to allow magnet carriers 264 and permanent magnets 266 to slide proximate to the tube openings 256 and therefore proximate to the tubes 220 for purposes discussed above with regard to permanent magnets 166. In this example, each tube block 254 includes a tube row, each having twelve openings 256. As discussed above, the extractor 202 includes eight tube blocks 254. Thus, the extractor 202 includes 96 openings 254.

The operation of the extractor 202 with respect to the system 100 is similar to that of extractor 102 discussed above, and will now be described with reference to FIGS. 1, 10–14 and 20–22. Initially, samples containing cells are provided in sample input tubes 112 (see FIG. 1). These samples may be of any type, including biological fluids such as blood, urine and cerebrospinal fluid, tissue homogenates and environmental samples, that are to be assayed for nucleic acids (DNA or RNA) of interest. After the start step 1000 (see FIG. 13), the robot 104 is first controlled in step 1010 to move to the pipette tip racks 108 to pick up a plurality of pipette tips, for example, four pipette tips (not shown). The robot 104 is then controlled to position the pipette tips over a respective number of sample tubes 112 and draw the samples into the respective pipette tips. The robot then moves the pipette tips over to the extractor 202, and releases the samples into respective sample tubes 220 that have been loaded in advance into the rack 218 positioned on the extractor 202.

Each sample tube 220 has been previously supplied with magnetically responsive particles 190 similar to those described above. Each of the sample tubes 112 also contains lyse solution which lyses the cell samples.

The above process continues until all of the samples from the sample input tubes 112 have been inserted into the corresponding tubes 220 in the extractor 202. It is noted that the number of samples drawn at each time (i.e., six samples in this example) can vary as desired. It is also noted that each time the robot draws its samples from sample tubes 112 into pipette tips and then dispenses those samples into corresponding tubes 220, the robot moves to a discard position to discard the pipette tips. The robot 104 then selects six new pipette tips to transfer six new samples from the input tubes 112 to the tubes 220.

Once all of the samples have been loaded into the respective sample tubes 220, the controller controls the resistive heating devices 255 in step 1020 to apply heat to the solutions in the tube 120 to lyse the samples. In this example, the solutions in the tubes 220 are heated to a temperature at or about 70° C. Once the lysing has been completed, the controller disables the resistive heating devices 255 to allow natural convection to cool the tube blocks 254, sample tubes 220 and solutions contained therein to a temperature less than the lysing temperature.

Once the lysing and cooling processes are completed, the robot 104 is controlled in step 1030 to transfer a suitable acidic solution, such as that described in U.S. Pat. No. 5,973,138, into the sample tubes 120. To do this, the robot 104 moves back and forth between the pipette tip racks 108, the bulk reagent containers 114, extractor 202, and the pipette disposal section (not shown) to transfer the acidic solution to, for example, six tubes 220 at a time. The robot 104 transfers acidic solution to six corresponding tubes 220. At this time, the controller controls the electromagnets 270 to generate an AC magnetic field, which demagnetizes the particles 190 so that the particles can freely mix with the acidic solution. In this example, the AC magnetic field is applied at a rate of at or about 60 times per second. The robot 104 then mixes the solution in the tubes 220 by drawing the solution into the pipette tips and discharging the solution back into the tubes 220 in a controlled manner, while raising and lowering the pipette tips into and out of the tubes 220 in a controlled manner to maintain minimum tip submersion.

Once the robot 104 has transferred acidic solution to six corresponding tubes 220 and has performed the mixing operations, the controller turns off the electromagnets to remove the AC magnetic field. The acidic solution that has been added to the cell sampling tube 220 causes the nucleic acid molecules to become bound to the magnetically responsive particles 190. Once the acidic solutions have been added to the samples in the sample tubes 220, the controller controls the stepper motor 226 in step 1040 to move the cam plates 224 in a direction indicated by arrow A in FIG. 10. This drives the shoulder screw 260 in an upward direction along fixed cam slots 258 so that the magnets 264 are positioned proximate to the tubes 220. Therefore, the molecule-bound particles 190 are attracted by the magnets 264 and become adherent to the sides of the tubes 220 as shown, for example, in FIG. 22.

The robot 104 is then controlled in step 1050 to use the pipette tips to remove the solution from the tubes 220 and discard the solution in a waste container (not shown). As in the operations discussed above, each time the robot 104 uses pipette tips to remove solution from respective tubes 220, the robot 104 discards the pipette tips and uses new pipette tips before repeating the process on the remaining tubes 220.

The robot 104 is then controlled in step 1060 to add a washing solution to each of the tubes 220. When the wash solution is being added to the tubes 220, the controller controls the cam plates 224 to move in the direction indicated by arrow B in FIGS. 11 and 12, which causes the shoulder screws 260 to drive the magnet carriers 264 and, hence the permanent magnets 266, in a downward direction in their respective fixed cam slots 258. When the magnets 266 are moved away from the tubes 220, the particles 190 are allowed to fall back into the bottoms of the tubes 220. At this time, the controller controls the electromagnets 270 in step 1070 to generate an AC magnetic field, which demagnetizes the particles 190 so that the particles can freely mix with the wash solution being added to the tubes 220. A rapid sequence of several (e.g., 5 to 30 or any suitable number) aspirate and dispense cycles is used to perform the mix the particles with the wash solution. Once the robot 104 has completed mixing the wash solution, the controller turns off the electromagnets 270 to remove the AC magnetic field.

After the wash solution has been added and mixed with the particles, the controller controls the stepper motor 226 in step 1080 to move the cam plates 224 in the direction along arrow A shown in FIG. 10, to drive the magnets 266 in the upward direction to be proximate to the tubes 220. The magnets 266 thus secure the molecule-bound particles 190 to the sides of the tubes again as shown in FIG. 22. The robot 104 is then controlled to use the pipette tips (not shown) to remove the wash solution from the tubes 220. This wash step may be repeated as many times as necessary to wash the particles, e.g., two times, as determined in step 1090.

The robot 104 is then controlled in step 1100 to add an elution reagent, such as those described in U.S. Pat. No. 5,973,138 referenced above, to the tubes 220. During this time, the controller controls the cam plates 224 to move in the direction indicated by arrow B in FIGS. 11 and 12, which causes the shoulder screws 260 to drive the magnet carriers 264 and, hence the permanent magnets 266, in a downward direction in their respective fixed cam slots 158. When the magnets 166 are moved away from the tubes 220, the particles 190 are allowed to fall back into the bottoms of the tubes 220 into the elution solution. The elution solution causes the molecules to become unbound from the particles 190. Also, the controller can controls the electromagnets 270 to generate an AC magnetic field, which demagnetizes the particles 190 so that the particles can freely mix with the elution solution being added to the tubes 220. In a manner similar to that described above, the robot 104 uses new pipette tips for each group of tubes 220 to which the elution solution is being added from the bulk reagent tank 114.

After the elution solution has been added to and mixed within all of the tubes 220, the stepper motor 226 is controlled in step 1120 to move the cam plates 224 along direction A, as shown in FIG. 10, to move the magnets 266 proximate to the tubes 220. The robot 104 is then controlled to use the pipette tips to transfer the elution solution containing the nucleic acid molecules that have been released from the particles 190 into priming wells and the microtiter trays 116.

Once all the samples have been transferred to the priming wells, the robot 104 uses fresh groups of pipette tips to transfer the samples to the amplification wells and microtiter trays (not shown). Once all the samples have been transferred into the amplification wells, the microtiter trays can be placed in a suitable reading device, such as the BDProbeTec™ ET system described above, and the process is completed in step 1140. In an alternative embodiment, the robot can transfer the samples directly from the priming wells to the amplification stage of the BDProbeTec™ ET system eliminating the need to move or convey microtiter trays.

Although only two exemplary embodiments of this invention has been described in detail above, those skilled in the art will readily appreciate that many modifications are possible in the exemplary embodiments without materially departing from the novel teachings and advantages of this invention. All such modifications are intended to be included within the scope of this invention as defined in the following claims.

What is claimed is:

1. A system for manipulating magnetically responsive particles having nucleic acid molecules bound thereto and being in a solution contained in at least one tube, said system comprising:

a tube receiver having at least one tube opening adapted to receive said tube therein;

at least one first magnet;

a magnet moving device, adapted to selectively move said first magnet between a first location with respect to said tube to attract said magnetically responsive particles toward an inner wall of said tube, and a second location with respect to said tube to allow said magnetically responsive particles to be suspended in said solution; and a second magnet, comprising an AC electromagnet, adapted to apply an AC magnetic field to said magnetically responsive particles when said first magnet is positioned at said second location, to remove a magnetization imposed on said magnetically responsive particles by said first magnet.

2. A system as claimed in claim 1, wherein:
said second magnet is substantially stationary with respect to said tube.

3. A system as claimed in claim 1, wherein:
said first and second magnets are disposed on substantially opposite sides of said tube.

4. A system as claimed in claim 1, wherein said magnet moving device comprises:
a cam and cam driver, said cam driver being adapted to drive said cam to move said first magnet between said first and second locations.

5. A system as claimed in claim 1, wherein said magnet moving device comprises:
at least one first panel having a first opening therein;
at least one second panel having at least one second opening therein, extending transverse to said first opening; and
an extension which is coupled to said first magnet and passes through said first and second opening;
said second panel being adapted to move with respect to said first panel to apply a driving force to said extension to cause said extension to move along said first and second openings between said first and second locations.

6. A system as claimed in claim 5 further comprising:
a motor, adapted to drive said second panel to move with respect to said first panel.

7. A system as claimed in claim 1, wherein:
said tube receiver has a plurality of said tube openings for receiving a plurality of said tubes therein;
said system comprises a plurality of said first magnets, each being positioned with respect to at least one of said tube openings; and
said magnet moving device is adapted to move said plurality of said first magnets between respective said first and second locations.

8. A system as claimed in claim 7 further comprising:
a plurality of second magnets, each being adapted to apply a magnetic field to said magnetically responsive particles in at least one of said tubes when a respective one of said first magnets is positioned at a respective said second location to substantially remove a magnetization imposed on said magnetically responsive particles by said respective first magnet.

9. A system as claimed in claim 1, further comprising:
a thermal element, adapted to at least one of apply thermal energy to said solution in said tube and extract thermal energy from said solution in said tube.

10. A system as claimed in claim 1, wherein:
said magnet moving device is adapted to move said magnet between said first and second locations in a first direction which is substantially parallel to a longitudinal axis of said tube.

11. A system as claimed in claim 1, further comprising:
at least one pair of said first magnets; and
wherein said magnet moving device is adapted to selectively move each said first magnet of said pair of first magnets between respective said first locations with respect to said tube to attract said magnetically responsive particles toward an inner wall of said tube, and respective said second locations with respect to said tube to allow said magnetically responsive particles to be suspended in said solution.

12. A system as claimed in claim 11, wherein:
said tube receiver has a plurality of said tube openings for receiving a plurality of said tubes therein;
said system comprises a plurality of said pairs of first magnets, each being positioned with respect to at least one of said tube openings; and
said magnet moving device is adapted to move said plurality of said pairs of first magnets between respective said first and second locations.

13. A system as claimed in claim 12, further comprising:
a plurality of second magnets, each being adapted to apply a magnetic field to said magnetically responsive particles in at least one of said tubes when a respective one of said pairs of said first magnets is positioned at a respective said second location to substantially remove a magnetization imposed on said magnetically responsive particles by said respective pair of said first magnets.

14. A system as claimed in claim 1, wherein:
said second magnet is disposed below a bottom of said tube opening.

15. A system for manipulating magnetically responsive particles having nucleic acid molecules bound thereto and being in a solution contained in at least one tube, said system comprising:
a tube receiver having at least one tube opening adapted to receive said tube therein;
at least one first magnet;
a magnet moving device, adapted to selectively move said first magnet between a first location with respect to said tube to attract said magnetically responsive particles toward an inner wall of said tube, and a second location with respect to said tube to allow said magnetically responsive particles to be suspended in said solution said magnet moving device comprising:
at least one first panel having a first opening therein;
at least one second panel having at least one second opening therein, extending transverse to said first opening; and
an extension which is coupled to said first magnet and passes through said first and second opening, said second panel being adapted to move with respect to said first panel to apply a driving force to said extension to cause said extension to move along said first and second openings between said first and second locations; and
a second magnet, adapted to apply a magnetic field to said magnetically responsive particles when said first magnet is positioned at said second location, to remove a magnetization imposed on said magnetically responsive particles by said first magnet.

16. A system as claimed in claim 15, further comprising:
a motor, adapted to drive said second panel to move with respect to said first panel.

* * * * *